(12) United States Patent
Desborough et al.

(10) Patent No.: US 10,779,754 B2
(45) Date of Patent: *Sep. 22, 2020

(54) GLYCEMIC HEALTH METRIC DETERMINATION AND APPLICATION

(71) Applicant: Medtronic Minimed, Inc., Northridge, CA (US)

(72) Inventors: Lane Desborough, Thousand Oaks, CA (US); Cesar C. Palerm, Pasadena, CA (US)

(73) Assignee: MEDTRONIC MINIMED, INC., Northridge, CA (US)

( * ) Notice: Subject to any disclaimer, the term of this patent is extended or adjusted under 35 U.S.C. 154(b) by 31 days.

This patent is subject to a terminal disclaimer.

(21) Appl. No.: 15/240,275

(22) Filed: Aug. 18, 2016

(65) Prior Publication Data

US 2016/0354019 A1 Dec. 8, 2016

Related U.S. Application Data

(62) Division of application No. 13/326,890, filed on Dec. 15, 2011, now Pat. No. 9,445,757.

(60) Provisional application No. 61/428,066, filed on Dec. 29, 2010.

(51) Int. Cl.
| | |
|---|---|
| *A61B 5/145* | (2006.01) |
| *G06F 19/00* | (2018.01) |
| *G16H 40/63* | (2018.01) |
| *G16H 50/30* | (2018.01) |
| *A61B 5/00* | (2006.01) |

(52) U.S. Cl.
CPC ........ *A61B 5/14532* (2013.01); *A61B 5/0002* (2013.01); *A61B 5/4839* (2013.01); *A61B 5/6849* (2013.01); *A61B 5/7225* (2013.01); *A61B 5/7275* (2013.01); *A61B 5/746* (2013.01); *G06F 19/3468* (2013.01); *G16H 40/63* (2018.01); *G16H 50/30* (2018.01)

(58) Field of Classification Search
None
See application file for complete search history.

(56) References Cited

U.S. PATENT DOCUMENTS

| | | |
|---|---|---|
| 5,391,250 A | 2/1995 | Cheney, II et al. |
| 6,254,586 B1 | 7/2001 | Mann et al. |
| 6,360,888 B1 | 3/2002 | McIvor et al. |
| | (Continued) | |

FOREIGN PATENT DOCUMENTS

WO  WO2011/157402 A1  12/2011

OTHER PUBLICATIONS

Keenan et al. (Journal of Diabetes Science and Technology, Sep. 2009, vol. 3, Iss. 5, 1207-1214).*

(Continued)

*Primary Examiner* — Olivia M. Wise
(74) *Attorney, Agent, or Firm* — Berkeley Law Technology Group, LLP

(57) ABSTRACT

Disclosed are methods, apparatuses, etc. for determination and application of a unidimensional metric for assessing a patient's glycemic health. In one particular implementation, a computed metric may be used to balance short-term and long-term risks associated with a particular therapy. In another implementation, a computed unidimensional metric may be used to balance risks of hyperglycemia and hypoglycemia.

13 Claims, 13 Drawing Sheets

(56) References Cited

U.S. PATENT DOCUMENTS

| | | |
|---|---|---|
| 6,424,847 B1 | 7/2002 | Mastrototaro et al. |
| 6,554,798 B1 | 4/2003 | Mann et al. |
| 6,558,320 B1 | 5/2003 | Causey, III et al. |
| 6,641,533 B2 | 11/2003 | Causey, III et al. |
| 6,895,263 B2 | 5/2005 | Shin et al. |
| 6,923,763 B1 | 8/2005 | Kovatchev |
| 7,204,823 B2 | 4/2007 | Estes et al. |
| 7,267,655 B1 | 9/2007 | Lyapko |
| 7,399,277 B2 | 7/2008 | Saidara et al. |
| 9,445,757 B2 | 9/2016 | Desborough |
| 10,390,740 B2 | 8/2019 | Desborough |
| 2006/0173406 A1 | 8/2006 | Hayes et al. |
| 2007/0016127 A1 | 1/2007 | Staib |
| 2007/0173710 A1 | 7/2007 | Petisce et al. |
| 2008/0157980 A1 | 7/2008 | Sachanandani |
| 2008/0221509 A1 | 9/2008 | Gottlieb et al. |
| 2008/0275384 A1 | 11/2008 | Mastrototaro |
| 2009/0171589 A1 | 7/2009 | Kovatchev |
| 2010/0106524 A1 | 4/2010 | Wu |
| 2010/0162786 A1 | 7/2010 | Keenan et al. |
| 2010/0168538 A1 | 7/2010 | Keenan et al. |
| 2010/0168539 A1 | 7/2010 | Palerm et al. |
| 2010/0204557 A1 | 8/2010 | Kiaie et al. |
| 2010/0324382 A1 | 12/2010 | Cantwell et al. |
| 2011/0071464 A1 | 3/2011 | Palem |
| 2011/0208155 A1 | 8/2011 | Palem et al. |
| 2011/0313390 A1 | 12/2011 | Roy et al. |
| 2013/0102867 A1 | 4/2013 | Desborough et al. |
| 2016/0354019 A1 | 12/2016 | Desborough et al. |
| 2020/0000384 A1 | 1/2020 | Desborough et al. |

OTHER PUBLICATIONS

Pickup et al. (Diabetes Care, 2002, 25, 593-598).*
Flood. Advances in Insulin Delivery Systems and Devices: Beyond the Vial and Syringe. Insulin 2006, vol. 1, No. 3, pp. 99-108 (Year: 2006).*
Cameron et al. "A Closed-Loop Artificial Pancreas Based on Risk Management", Journal of Diabetes Science and Technology, vol. 5, Issue 2, Mar. 2011, pp. 368-379.
Desborough et al. "Performance Assessment Measures for Univariate Feedback Control", The Canadian Journal of Chemical Engineering, vol. 70, Dec. 1992, pp. 1186-1195.
Kovatchev et al. "Control to Range for Diabetes: Functionality and Modular Architecture", Journal of Diabetes Science and Technology, vol. 3, Issue 5, Sep. 2009, pp. 1058-1068.
Hovorka et al. "Nonlinear Model Predictive Control of Glucose Concentration in Subjects with type 1 Diabetes", Institute of Physics Publishing, 2004, pp. 905-920.
Mudaliar et al. "Insulin Aspart (1328-Asp-Insulin); A Fast-Acting Analog of Human Insulin", Diabetes care, vol. 22, No. 9, Sep. 1999, pp. 1501-1506.
Magni et al. "Run-to-Run Tuning of Model Predictive Control for Type 1 Diabetes Subjects: In Silico Trial", Journal of diabetes Science and Technology, vol. 3, Issue 5, Sep. 2009, pp. 1091-1098.
Van Den Berghe et al. "Intensive Insulin Therapy in Critically Ill patients", The New England Journal of Medicine, vol. 45, No. 19, Nov. 8, 2001, pp. 1359-1367.
U.S. Appl. No. 13/326,890, filed Dec. 15, 2011, 67 Pages.
U.S. Appl. No. 13/326,890 / Notice of Publication, dated Jun. 22, 2012, 1 Page.
U.S. Appl. No. 13/326,890 / Requirement for Restriction/Election, dated Dec. 16, 2014, 7 pages.
U.S. Appl. No. 13/326,890 / Response to Election and Amendments, filed Feb. 12, 2015, 10 pages.
U.S. Appl. No. 13/326,890 / Non-Final Rejection, dated Jun. 2, 2015, 9 pages.
U.S. Appl. No. 13/326,890 / Amendment after non-final, dated Aug. 31, 2015, 18 pages.
U.S. Appl. No. 13/326,890 / Final rejection, dated Dec. 22, 2015, 17 pages.
U.S. Appl. No. 13/326,890 / Applicant Interview, dated Feb. 17, 2016, 3 pages.
U.S. Appl. No. 13/326,890 / Amendment after final, dated Mar. 16, 2016.
U.S. Appl. No. 13/326,890 / Notice of Allowance and Fees, dated May 18, 2016, 11 pages.
U.S. Appl. No. 13/326,890 / Issue Fee Payment and Rule 312 Amendment, dated Aug. 17, 2016, 4 pages.
U.S. Appl. No. 13/326,890 / Response to Amendment under Rule 312, dated Aug. 24, 2016, 1 page.
U.S. Appl. No. 13/326,890 / Issue Notification, dated Aug. 31, 2016, 1 page.
U.S. Appl. No. 13/710,122, filed Dec. 10, 2012, 74 Pages.
U.S. Appl. No. 13/710,122 / Notice of Publication, dated Apr. 25, 2013, 1 Page.
U.S. Appl. No. 13/710,122 / Non-Final Rejection, dated Jun. 24, 2015, 15 Pages.
U.S. Appl. No. 13/710,122 / Amendment/Req. Reconsideration-After Non-Final Rejection, dated Sep. 18, 2015, 20 pages.
U.S. Appl. No. 13/710,122 / Final Rejection, dated Dec. 31, 2015, 11 pages.
U.S. Appl. No. 13/710,122 / Response After Final Action, dated Feb. 24, 2016, 31 pages.
U.S. Appl. No. 13/710,122 / RCE, dated Apr. 26, 2016, 19 pages.
U.S. Appl. No. 13/710,122 / Non-Final Rejection, dated Jul. 12, 2016, 12 pages.
U.S. Appl. No. 13/710,122 / Amendment/Req. Reconsideration—After Non-Final Reject, dated Nov. 7, 2016, 27 pages.
PCT/US2011/065402: Application as filed Dec. 16, 2011, 64 pages.
PCT/US2011/065402: International search report and written opinion, dated Jun. 11, 2012, 18 pages.
PCT/US2011/065402: IPRP, dated Jul. 2, 2013, 11 pages.
SIPO CN App. No. 201180063434: First Office Action, translated, dated Aug. 4, 2015, 13 pages.
SIPO CN App. No. 201180063434: Second Office Action, translated, dated Mar. 20, 2015, 18 pages.
SIPO CN App. No. 201180063434: Notification to Grant Patent Right for Invention, translated, dated Aug. 13, 2015, 3 pages.
EP 11808478.9 / Rule 161 Communication, dated Aug. 6, 2013, 2 pages.
EP 11808478.9 / Response to Rule 161 Communication, dated Feb. 13, 2014, 17 pages.
EP 11808478.9 / Examiner's Report, dated Feb. 6, 2018, 6 pages.
U.S. Appl. No. 13/710,122 / Final Rejection, dated Nov. 16, 2017, 11 pages.
U.S. Appl. No. 13/710,122 / Advisory Action, dated Feb. 26, 2018, 3 pages.
U.S. Appl. No. 13/710,122 / RCE and Amendments, dated Mar. 23, 2018, 18 pages.
CA App. 2,818,677 / Amendment, dated Apr. 13, 2018, 10 pages.
U.S. Appl. No. 13/710,122 / Response After Final Action, dated Jan. 16, 2018, 13 pages.
CA App. 2,818,677 / Examiner's report dated Oct. 16, 2017, 4 pages.
U.S. Appl. No. 13/326,890 / Declaration of Cesar Palerm, Mar. 11, 2016, 31 pages.
U.S. Appl. No. 13/710,122 / Non-Final Rejection, dated Apr. 3, 2017, 12 pages.
U.S. Appl. No. 13/710,122 / Amendment/Req. Reconsideration-After Non-Final Reject, dated Jun. 28, 2017.
U.S. Appl. No. 13/710,122 / Non-Final Rejection, dated Jun. 8, 2018, 12 pages.
U.S. Appl. No. 13/710,122 / Amendment, filed Jun. 25, 2018, 13 pages.
Response to Art. 94(3) Communication, dated Jun. 14, 2018, (16 pages); EP App. 11808478.9.
CA App. 2,818,677 / Examiner's Report, dated Oct. 9, 2018, 3 pages.
U.S. Appl. No. 13/710,122 / Response as Filed Mar. 1, 2019, 12 pages.
U.S. Appl. No. 13/710,122 / Non-Final Office Action, dated Dec. 11, 2018, 5 pages.
CA App. 2,818,677 / Amendment, dated Dec. 20, 2018, 14 pages.

(56) References Cited

OTHER PUBLICATIONS

U.S. Appl. No. 13/710,122 / Notice of allowance and Fees Due, dated Apr. 8, 2019, 8 pages.
EP 11808478.9 / Notice of intention to Grant, dated Mar. 27, 2019, 5 pages.
EP 11808478.9 / Text proposed for grant, clean copy, dated Mar. 27, 2019, 44 pages.
EP 11808478.9 / Text proposed for grant, marked up copy, dated Mar. 27, 2019, 44 pages.
Issue Notification, dated Aug. 7, 2019, U.S. Appl. No. 13/710,122, 1 pg.
U.S. Appl. No. 16/508,196, filed Jul. 10, 2019, 65 pgs.
Preliminary Amendment, filed Jul. 10, 2019, U.S. Appl. No. 16/508,196, 8 pgs.
Transmittal of New European Patent Application, Divisional of European Patent Application No. 11808478.9, sent Jul. 24, 2019, 9 pgs.
EP Patent Application No. EP19188220.8, filed Jul. 24, 2019, 50 pgs.
Acknowledgement of Receipt, EP Patent Application No. EP19188220.8, dated Jul. 24, 2019, 2 pgs.
Notice to File Corrected Application Papers, dated Jul. 25, 2019, U.S. Appl. No. 16/508,196, 3 pgs.
U.S. Appl. No. 16/508,196 / Application and Preliminary Amendment as filed on Jul. 10, 2019, 85 pages.
U.S. Appl. No. 16/508,196 / Filing Receipt and Notice to File Corrected Application Papers, Jul. 25, 2019, 5 pages.
U.S. Appl. No. 16/508,196 / Applicant Response to Pre-Exam Formalites Notice, Sep. 17, 2019, 96 pages.
U.S. Appl. No. 16/508,196 / Applicant Response to Pre-Exam Formalities Notice, Sep. 23, 2019, 2 pages.
CA Appl'n. 2,818,677 / Office Action, dated Jul. 11, 2019, 4 pages.
CA 2818677 / Office Action dated Jul. 11, 2019, 4 pages.
EP 19188220.8 / Extended European Search Report—Rule 62 Communication dated Oct. 31, 2019, 9 pages.
EP 19188220.8 / Article 67(3) Notification of European Publication dated Nov. 6, 2019, 2 pages.

\* cited by examiner

| | | | Hypo-strong | | | Hypo-weak | | Balanced | | | Hyper-weak | | Hyper-strong | | | | | | | |
|---|---|---|---|---|---|---|---|---|---|---|---|---|---|---|---|---|---|---|---|---|
| | | | %Hypo | LBGI | AUC (hypo) | IGC1 | CV | Fraser | RI | IGC2 | SD | IQR | M-Value | GRADE | AUC | AUC (hyper) | J-Index | HBGI | %Hyper | Mean | A1c |
| Hypo-strong | %Hypo | | 1.0 | 1.0 | 1.0 | 0.6 | 0.5 | 0.2 | 0.0 | 0.0 | -0.2 | -0.2 | -0.3 | -0.4 | -0.5 | -0.6 | -0.6 | -0.6 | -0.8 | -0.8 | -0.8 |
| | LBGI | | 1.0 | 1.0 | 1.0 | 0.6 | 0.4 | 0.2 | 0.0 | -0.1 | -0.2 | -0.3 | -0.4 | -0.5 | -0.6 | -0.6 | -0.6 | -0.7 | -0.8 | -0.8 | -0.8 |
| | AUC (hypo) | | 1.0 | 1.0 | 1.0 | 0.7 | 0.6 | 0.3 | 0.1 | 0.1 | -0.1 | -0.1 | -0.2 | -0.3 | -0.4 | -0.5 | -0.5 | -0.5 | -0.7 | -0.7 | -0.7 |
| Hypo-weak | IGC1 | | 0.6 | 0.6 | 0.7 | 1.0 | 0.8 | 0.9 | 0.8 | 0.7 | 0.5 | 0.4 | 0.5 | 0.4 | 0.2 | 0.1 | 0.1 | 0.1 | -0.1 | -0.1 | -0.1 |
| | CV) | | 0.5 | 0.4 | 0.6 | 0.8 | 1.0 | 0.7 | 0.7 | 0.7 | 0.8 | 0.7 | 0.6 | 0.5 | 0.4 | 0.4 | 0.4 | 0.4 | 0.1 | 0.1 | 0.1 |
| Balanced | Fraser | | 0.2 | 0.2 | 0.3 | 0.9 | 0.7 | 1.0 | 1.0 | 1.0 | 0.7 | 0.7 | 0.8 | 0.7 | 0.6 | 0.5 | 0.5 | 0.5 | 0.3 | 0.3 | 0.3 |
| | RI | | 0.0 | 0.0 | 0.1 | 0.8 | 0.7 | 1.0 | 1.0 | 1.0 | 0.8 | 0.8 | 0.9 | 0.9 | 0.8 | 0.7 | 0.7 | 0.7 | 0.5 | 0.5 | 0.5 |
| | IGC2 | | -0.3 | -0.1 | 0.1 | 0.7 | 0.7 | 1.0 | 1.0 | 1.0 | 0.8 | 0.8 | 0.9 | 0.9 | 0.8 | 0.7 | 0.7 | 0.7 | 0.6 | 0.5 | 0.5 |
| Hyper-weak | SD | | -0.2 | -0.2 | -0.1 | 0.5 | 0.8 | 0.7 | 0.8 | 0.8 | 1.0 | 1.0 | 0.9 | 0.9 | 0.9 | 0.9 | 0.9 | 0.9 | 0.7 | 0.7 | 0.7 |
| | IQR | | -0.2 | -0.3 | -0.1 | 0.4 | 0.7 | 0.7 | 0.8 | 0.8 | 1.0 | 1.0 | 0.9 | 0.9 | 0.9 | 0.9 | 0.9 | 0.9 | 0.8 | 0.8 | 0.8 |
| Hyper-strong | M-Value | | -0.3 | -0.4 | -0.2 | 0.5 | 0.6 | 0.8 | 0.9 | 0.9 | 0.9 | 0.9 | 1.0 | 1.0 | 1.0 | 0.9 | 0.9 | 0.9 | 0.8 | 0.8 | 0.8 |
| | GRADE | | -0.4 | -0.5 | -0.3 | 0.4 | 0.5 | 0.7 | 0.9 | 0.9 | 0.9 | 0.9 | 1.0 | 1.0 | 1.0 | 0.9 | 0.9 | 0.9 | 0.9 | 0.8 | 0.8 |
| | AUC | | -0.5 | -0.6 | -0.4 | 0.2 | 0.4 | 0.6 | 0.8 | 0.8 | 0.9 | 0.9 | 1.0 | 1.0 | 1.0 | 1.0 | 1.0 | 1.0 | 0.9 | 0.9 | 0.9 |
| | AUC(hyper) | | -0.6 | -0.6 | -0.5 | 0.1 | 0.4 | 0.5 | 0.7 | 0.7 | 0.9 | 0.9 | 0.9 | 0.9 | 1.0 | 1.0 | 1.0 | 1.0 | 1.0 | 1.0 | 1.0 |
| | J-Index | | -0.6 | -0.6 | -0.5 | 0.1 | 0.4 | 0.5 | 0.7 | 0.7 | 0.9 | 0.9 | 0.9 | 0.9 | 1.0 | 1.0 | 1.0 | 1.0 | 1.0 | 1.0 | 1.0 |
| | HBGI | | -0.6 | -0.7 | -0.5 | 0.1 | 0.4 | 0.5 | 0.7 | 0.7 | 0.9 | 0.9 | 0.9 | 0.9 | 1.0 | 1.0 | 1.0 | 1.0 | 1.0 | 1.0 | 1.0 |
| | %Hyper | | -0.8 | -0.8 | -0.7 | -0.1 | 0.1 | 0.3 | 0.5 | 0.6 | 0.7 | 0.8 | 0.8 | 0.9 | 0.9 | 1.0 | 1.0 | 1.0 | 1.0 | 1.0 | 1.0 |
| | Mean | | -0.8 | -0.8 | -0.7 | -0.1 | 0.1 | 0.3 | 0.5 | 0.5 | 0.7 | 0.8 | 0.8 | 0.8 | 0.9 | 1.0 | 1.0 | 1.0 | 1.0 | 1.0 | 1.0 |
| | A1c | | -0.8 | -0.8 | -0.7 | -0.1 | 0.1 | 0.3 | 0.5 | 0.5 | 0.7 | 0.8 | 0.8 | 0.8 | 0.9 | 1.0 | 1.0 | 1.0 | 1.0 | 1.0 | 1.0 |

*FIG. 1*

| Metric | Loss Function g(x) [mg/dl] | Loss Function g(x) [mg/l] |
|---|---|---|
| Mean ($\mu$) | $g(x) = x$ | $g(x) = x$ |
| Variance ($\sigma^2$) | $g(x) = (x - \mu)^2$ | $g(x) = (x-\mu)^2$ |
| $A_{1c}$ (est.)[1] | $g(x) = \dfrac{x + 46.7}{28.7}$ | $g(x) = \dfrac{18x + 46.7}{28.7}$ |
| AUC | $g(x) = \begin{cases} 70 - x & \text{if } x \leq 70 \\ 0 & \text{if } 70 < x < 140 \\ 0 & \text{otherwise} \end{cases}$ | $g(x) = \begin{cases} 3.9 - x & \text{if } x \leq 3.9 \\ 0 & \text{if } 3.9 < x < 7.8 \\ x - 7.8 & \text{if } x \geq 7.8 \end{cases}$ |
| AUC (Hypo) | $g(x) = \begin{cases} 70 - x & \text{if } x \leq 70 \\ 0 & \text{otherwise} \end{cases}$ | $g(x) = \begin{cases} 3.9 - x & \text{if } x \leq 3.9 \\ 0 & \text{otherwise} \end{cases}$ |
| AUC (Hyper) | $g(x) = \begin{cases} x - 140 & \text{if } x \geq 140 \\ 0 & \text{otherwise} \end{cases}$ | $g(x) = \begin{cases} x - 7.8 & \text{if } x \geq 7.8 \\ 0 & \text{otherwise} \end{cases}$ |
| $ICG_1$ | $g(x) = \begin{cases} \dfrac{(80-x)^2}{30} & \text{if } x < 80 \\ 0 & \text{if } 80 \leq x \leq 140 \\ \dfrac{(x-140)^{1.1}}{30} & \text{if } x \geq 140 \end{cases}$ | $g(x) = \begin{cases} \dfrac{(80-18x)^2}{30} & \text{if } x < 4.44 \\ 0 & \text{if } 4.44 \leq x \leq 7.78 \\ \dfrac{(18x-140)^{1.1}}{30} & \text{if } x \geq 7.78 \end{cases}$ |
| $ICG_2$ | $g(x) = \begin{cases} \dfrac{(80-x)^{1.9}}{30} & \text{if } x < 80 \\ 0 & \text{if } 80 \leq x \leq 140 \\ \dfrac{(x-140)^{1.35}}{30} & \text{if } x \geq 140 \end{cases}$ | $g(x) = \begin{cases} \dfrac{(80-18x)^{1.9}}{30} & \text{if } x < 4.44 \\ 0 & \text{if } 4.44 \leq x \leq 7.78 \\ \dfrac{(18x-140)^{1.35}}{30} & \text{if } x \geq 7.78 \end{cases}$ |
| GRADE | $g(x) = \min\left(50, 425\left(\log_{10}\left(\log_{10}\left(\dfrac{x}{18}\right)\right) + 0.16\right)^2\right)$ | $g(x) = \min\left(50, 425\left(\log_{10}\left(\log_{10}(x)\right) + 0.16\right)^2\right)$ |
| % Hypo | $g(x) = \begin{cases} 100 & \text{if } x \leq 70 \\ 0 & \text{otherwise} \end{cases}$ | $g(x) = \begin{cases} 100 & \text{if } x \leq 3.9 \\ 0 & \text{otherwise} \end{cases}$ |
| % Hyper | $g(x) = \begin{cases} 100 & \text{if } x \geq 140 \\ 0 & \text{otherwise} \end{cases}$ | $g(x) = \begin{cases} 100 & \text{if } x \geq 7.8 \\ 0 & \text{otherwise} \end{cases}$ |
| Risk Index | $g(x) = 10\left(1.509\left((\log(x))^{1.084} - 5.381\right)\right)^2$ | $g(x) = 10\left(1.794\left((\log(x))^{1.026} - 1.861\right)\right)^2$ |
| LBGI | $g(x) = \begin{cases} 10\left(1.509\left((\log(x))^{1.084} - 5.381\right)\right)^2 & x < 112.47 \\ 0 & \text{otherwise} \end{cases}$ | $g(x) = \begin{cases} 10\left(1.794\left((\log(x))^{1.026} - 1.861\right)\right)^2 & x < 6.249 \\ 0 & \text{otherwise} \end{cases}$ |
| HBGI | $g(x) = \begin{cases} 10\left(1.509\left((\log(x))^{1.084} - 5.381\right)\right)^2 & x > 112.47 \\ 0 & \text{otherwise} \end{cases}$ | $g(x) = \begin{cases} 10\left(1.794\left((\log(x))^{1.026} - 1.861\right)\right)^2 & x > 6.249 \\ 0 & \text{otherwise} \end{cases}$ |
| Fraser | $g(x) = 0.2096x - 26 + \begin{cases} 6 \times 10^{-5}(146.8-x)^3 & \text{if } x \leq 146.8 \\ 0 & \text{otherwise} \end{cases}$ | $g(x) = 3.7728x - 26 + \begin{cases} 0.35(8.156-x)^3 & \text{if } x \leq 8.156 \\ 0 & \text{otherwise} \end{cases}$ |
| M-Value | $g(x) = \left\|10 \log_{10}\left(\dfrac{x}{100}\right)\right\|^3$ | $g(x) = \left\|10 \log_{10}(0.18x)\right\|^3$ |
| Log-Square | $g(x) = \left(\log_{10}\left(\dfrac{x}{120}\right)\right)^2$ | $g(x) = \left(\log_{10}\left(\dfrac{18x}{120}\right)\right)^2$ |

FIG. 4

| | % Hypo | LBGI | AUC (hypo) | IGC1 | CV | Log-Square | Fraser | RI | IGC2 | SD | IQR | M-Value | GRADE | AUC | AUC (hyper) | J-Index | HBGI | %Hyper | Mean |
|---|---|---|---|---|---|---|---|---|---|---|---|---|---|---|---|---|---|---|---|
| Log-Square (Gc = 119.5 mg/dL) | 0.3 | 0.2 | 0.4 | 0.9 | 0.8 | 1.0 | 1.0 | 0.9 | 0.9 | 0.7 | 0.6 | 0.7 | 0.7 | 0.5 | 0.4 | 0.4 | 0.4 | 0.3 | 0.2 |
| Log-Square (Gc = 120 mg/dL) | 0.3 | 0.3 | 0.4 | 0.9 | 0.8 | 1.0 | 1.0 | 0.9 | 0.9 | 0.7 | 0.6 | 0.7 | 0.6 | 0.5 | 0.4 | 0.4 | 0.4 | 0.2 | 0.2 |

*FIG. 5*

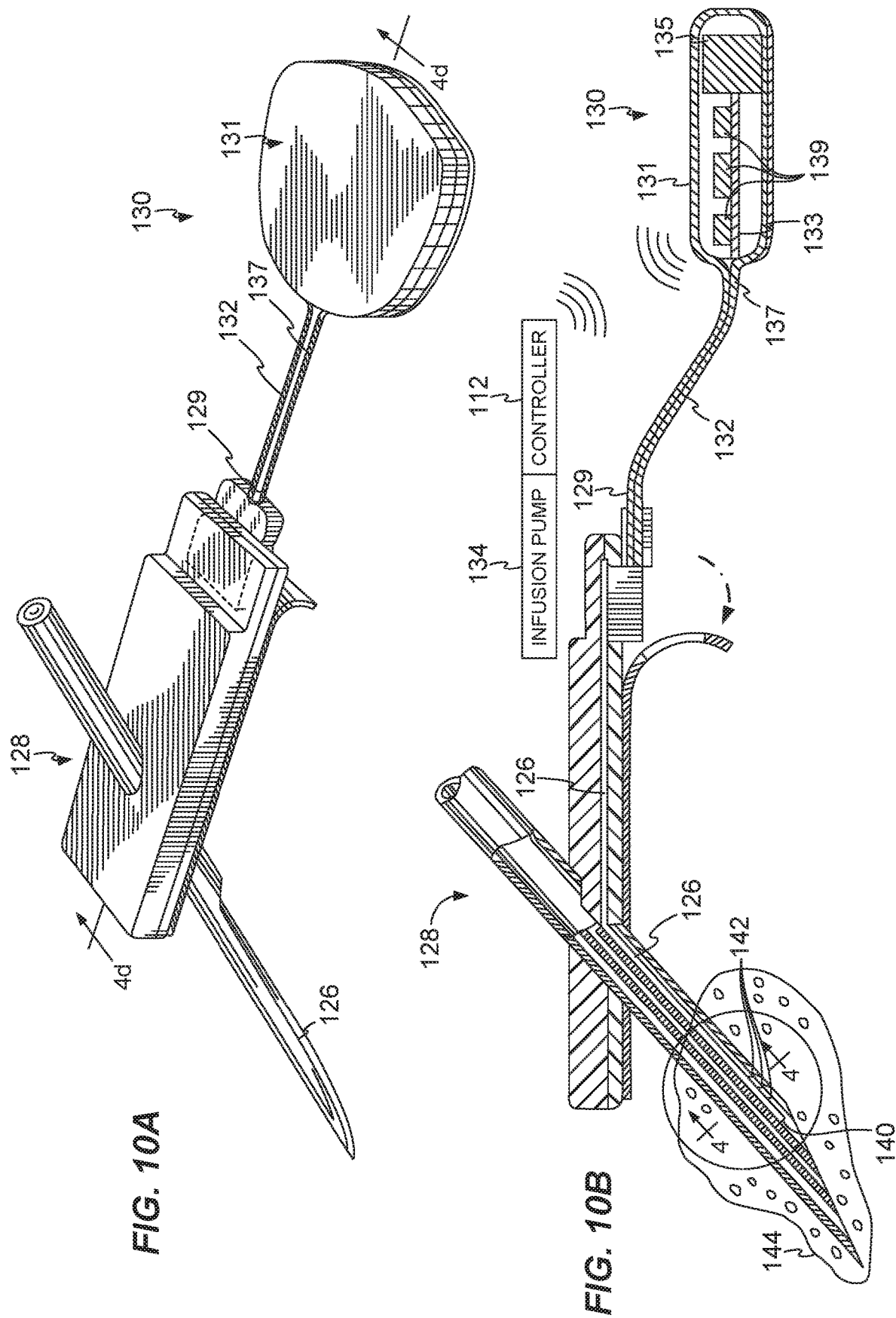

GLYCEMIC HEALTH METRIC DETERMINATION AND APPLICATION

This application claims the benefit of priority to U.S. Provisional Patent Appl. No. 61/428,066 titled "QUANTIFYING GLYCEMIC CONTROL USING LOG-SQUARE METRIC," filed on Dec. 29, 2010, and U.S. Nonprovisional patent application Ser. No. 13/326,890 titled "GLYCEMIC HEALTH METRIC DETERMINATION AND APPLICATION," filed on Dec. 15, 2011, both of which assigned to the assignee of claimed subject matter, and incorporated herein by reference in its entirety.

BACKGROUND

1. Field

Subject matter disclosed herein relates to techniques to determine a metric quantifying a glycemic health of a patient.

2. Information

The pancreas of a normal healthy person produces and releases insulin into the blood stream in response to elevated blood plasma glucose levels. Beta cells (β-cells), which reside in the pancreas, produce and secrete insulin into the blood stream as it is needed. If β-cells become incapacitated or die, which is a condition known as Type 1 diabetes mellitus (or in some cases, if β-cells produce insufficient quantities of insulin, a condition known as Type 2 diabetes), then insulin may be provided to a body from another source to maintain life or health.

Traditionally, because insulin cannot be taken orally, insulin has been injected with a syringe. More recently, the use of infusion pump therapy has been increasing in a number of medical situations, including for delivering insulin to diabetic individuals. For example, external infusion pumps may be worn on a belt, in a pocket, or the like, and they can deliver insulin into a body via an infusion tube with a percutaneous needle or a cannula placed in subcutaneous tissue.

To determine an appropriate therapy for treating a patient's diabetic conditions, a blood glucose concentration is typically measured using one or more techniques such as, for example, metered blood glucose measurements (e.g. using finger sticks) or continuous glucose monitoring from processing signals generated by a blood glucose sensor inserted into subcutaneous tissue. While contemporaneous measurements of blood glucose concentration may be an effective metric for determining an appropriate therapy for addressing an immediate condition (e.g., determining a size of an insulin bolus to be given to a patient), measurements of blood glucose alone do not necessarily provide an indication of a patient's glycemic health over a time period, for example. Other metrics for assessing a patients' overall glycemic health may include a measurement of hemoglobin A1c (or HbA1c), which is one form of glycohemoglobin. Here, such a hemoglobin is irreversibly glycated at one or both N-terminal valine residues of a β-chain of hemoglobin A0. Glycation of hemoglobin in a patient is typically quantified as a percentage of total hemoglobin.

A strong relationship exists between hemoglobin A1c levels in a diabetes patient and risks of micro-vascular complications. Accordingly, hemoglobin A1c measurements have become an integral component of the treatment of diabetes patients.

SUMMARY

Briefly, example embodiments may relate to methods, systems, apparatuses, and/or articles, etc. for a method comprising: at a special purpose computing apparatus, computing a profile of a blood glucose concentration of a patient based, at least in part, on observations of said blood glucose concentration collected at a blood glucose monitoring device; applying a cost or loss function to said computed profile to compute a metric representative of a glycemic health of the patient, said cost or loss function being based, at least in part, on a log-square metric; and affecting a therapy applied to said patient based, at least in part, on said computed metric. The computed metric may comprise a unidimensional metric in a particular embodiment. In another embodiment, affecting the therapy may comprise setting a target blood glucose level or target blood glucose range of said patient based, at least in part, on the computed metric. In one alternative implementation, the method may further comprise triggering an alarm in response to said computed metric.

In another implementation, the blood glucose concentration profile may comprise an estimated probability distribution function. Alternatively, the blood glucose concentration profile may comprise a histogram of blood glucose concentration measurements. In yet another alternative, the blood glucose concentration profile may comprise blood glucose concentration measurements. In another implementation, the log-square metric has the form:

$$g(x) = \left[\log\left(\frac{x}{G_c}\right)\right]^2$$

In another implementation, the computed metric may comprise a bi-dimensional metric, and the method may further comprise: applying a first portion of said loss or cost function to said blood glucose concentration profile to derive a hyperglycemia component of said computed metric; and applying a second portion of said loss or cost function to said blood glucose concentration to derive a hypoglycemia component of said computed metric.

In another implementation, the method further comprises: defining the blood glucose concentration profile for a recurring period; computing the metric based, at least in part, on the recurring period; and affecting the therapy for the recurring period in the future based, at least in part, on the computed metric. Here, the recurring period may comprise a time of day. Alternatively, the recurring period may comprise a day of week. In another embodiment, defining the blood glucose concentration profile for a recurring period further comprises computing the profile for the recurring period based on observations of said blood glucose concentration collected only during said recurring period.

In a particular implementation, affecting the therapy applied to said patient further comprises affecting a closed-loop insulin delivery system based, at least in part, on said computed metric. For example, affecting the closed-loop insulin delivery system may further comprise affecting periodic command based, at least in part, on the computed metric.

In another implementation, an apparatus may comprise one or more processors to: for a plurality of patients, determine an associated plurality of unidimensional metrics indicative of glycemic health of the patients, said unidimensional metrics being computed based, at least in part, on an application of a cost or loss function to profiles of blood glucose concentration of said patients; and rank the patients for treatment according to a triage policy based, at least in part, on the unidimensional metrics. In one alternative aspect, the apparatus may further comprise communication interface components to receive information from a communication network, the one or more processors further to: compute said unidimensional metrics based, at least in part, on messages received through said communication interface components from computing platforms co-located with said patients. In a particular implementation, the messages may comprise measurements of blood glucose concentration collected at glucose monitoring devices. Alternatively, the messages may comprise unidimensional metrics computed at the computing platforms co-located with the patients.

In another embodiment, an article comprises a non-transitory storage medium comprising machine-readable instructions stored thereon which are executable by a special purpose computing apparatus to: determine an associated plurality of unidimensional metrics indicative of glycemic health of the patients, the unidimensional metrics being computed based, at least in part, on an application of a cost or loss function to profiles of blood glucose concentration of the patients; and rank the patients for treatment according to a triage policy based, at least in part, on the unidimensional metrics.

In another embodiment, an article comprises a non-transitory storage medium comprising machine-readable instructions stored thereon which are executable by a special purpose computing apparatus to: compute a profile of a blood glucose concentration of a patient based, at least in part, on observations of the blood glucose concentration collected at a blood glucose monitoring device; apply a cost or loss function to the computed profile to compute a metric representative of a glycemic health of the patient, the cost or loss function being based, at least in part, on a log-square metric; and affect a therapy applied to the patient based, at least in part, on the computed metric. In a particular implementation, the instructions are executable by the special purpose computing apparatus to affect the therapy by generating commands in an infusion system.

In another embodiment, an article comprises a non-transitory storage medium comprising machine-readable instructions stored thereon which are executable by a special purpose computing apparatus to: for a plurality of patients, determine an associated plurality of unidimensional metrics indicative of glycemic health of the patients, the unidimensional metrics being computed based, at least in part, on an application of a cost or loss function to profiles of blood glucose concentration of said patients; and rank the patients for treatment according to a triage policy based, at least in part, on said unidimensional metrics.

In another implementation, an apparatus comprises: means for computing a profile of a blood glucose concentration of a patient based, at least in part, on observations of said blood glucose concentration; means for applying a cost or loss function to said computed profile to compute a metric representative of a glycemic health of the patient, the cost or loss function being based, at least in part, on a log-square metric; and means for affecting a therapy applied to said patient based, at least in part, on the computed metric.

In another embodiment, an apparatus comprises: for a plurality of patients, means for determining an associated plurality of unidimensional metrics indicative of glycemic health of the patients, said unidimensional metrics being computed based, at least in part, on an application of a cost or loss function to profiles of blood glucose concentration of the patients; and means for ranking the patients for treatment according to a triage policy based, at least in part, on the unidimensional metrics.

In another embodiment, a method comprises: at a special purpose computing apparatus, for a plurality of patients, determining an associated plurality of unidimensional metrics indicative of glycemic health of the patients, the unidimensional metrics being computed based, at least in part, on an application of a cost or loss function to profiles of blood glucose concentration of the patients, the profiles of blood glucose concentration being obtained for the patients under multiple predefined therapies; and ranking the predefined therapies based, at least in part, on the unidimensional metrics. In one particular implementation, the predefined therapies are defined, at least in part, by closed-loop system design features.

Other alternative example embodiments are described herein and/or illustrated in the accompanying Drawings. Additionally, particular example embodiments may be directed to an article comprising a storage medium including machine-readable instructions stored thereon which, if executed by a special purpose computing device and/or processor, may be directed to enable the special purpose computing device/processor to execute at least a portion of described method(s) according to one or more particular implementations. In other particular example embodiments, a sensor may be adapted to generate one or more signals responsive to a measured blood glucose concentration in a body while a special purpose computing device and/or processor may be adapted to perform at least a portion of described method(s) according to one or more particular implementations based upon the one or more signals generated by the sensor.

BRIEF DESCRIPTION OF THE FIGURES

Non-limiting and non-exhaustive features are described with reference to the following figures, wherein like reference numerals refer to like and/or analogous parts throughout the various figures:

FIG. 1 is table showing Spearman ranking coefficients according to an embodiment;

FIG. 4 is a table of alternative cost or loss functions applicable to a blood glucose concentration profile for computing a metric indicative of glycemic health according to alternative embodiments;

FIG. 5 is a table of Spearman rank coefficients for use in balancing three hypoglycemic-biased metrics and three hyperglycemic-biased metrics for use in determining a cost or loss function according to an embodiment;

FIG. 10(a) is a perspective view of an example glucose sensor system for use in accordance with an embodiment.

FIG. 10(b) is a side cross-sectional view of a glucose sensor system of FIG. 10(a) for an embodiment.

DETAILED DESCRIPTION

Figure 2:
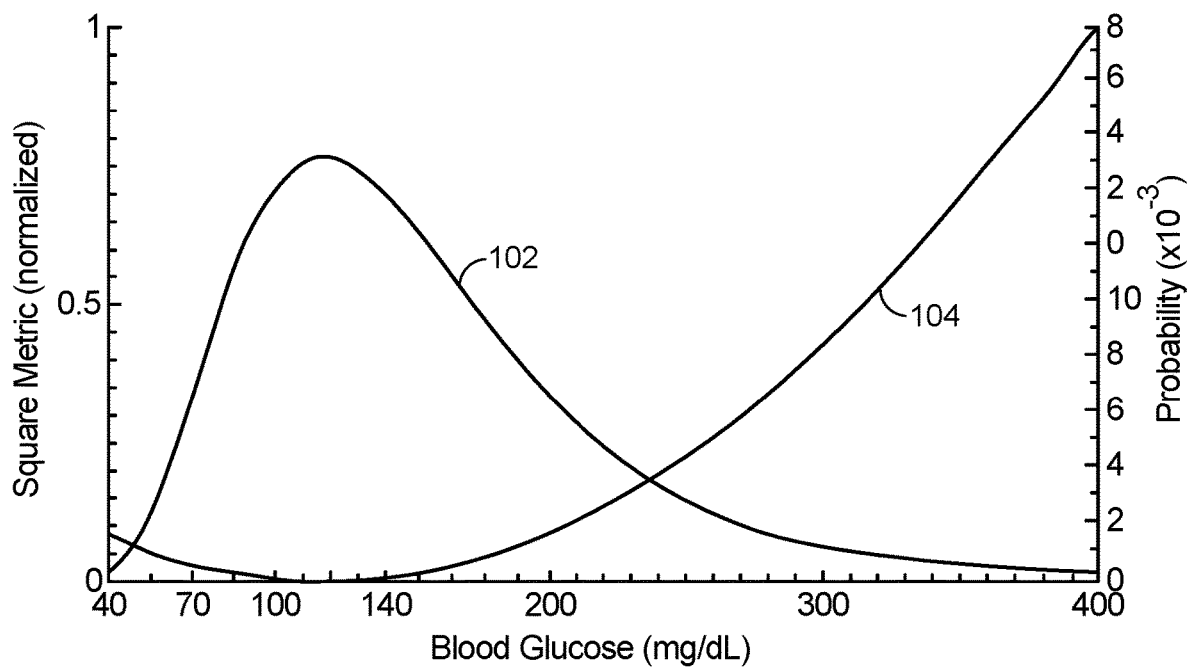
FIG. 2 is a plot of a profile of a blood glucose concentration laid over a cost or loss function according to an embodiment.

As discussed above, contemporaneous measurements of a blood glucose concentration in a patient may be used for determining an insulin therapy for treating the patient's diabetic condition. Measurements of a blood glucose concentration may be useful in determining an insulin therapy for treating a diabetic's immediate condition. Measurements of blood glucose alone, however, may not completely characterize the patient's glycemic health, or take into consideration any possible long-term effects from application of a particular insulin therapy over a time period, for example.

In particular embodiments of insulin therapy infusion of insulin may be controlled so as to control/maintain a patient's blood glucose concentration at a target level or within a target range, thus reducing the risk that a patient's blood glucose level transition to dangerous extreme levels. Maintaining a patient's blood glucose concentration at a target level or within a target range may reduce the risk of hypoglycemia or hyperglycemia if a patient, non-medical professional or medical professional is not fully attentive to acting to affect a system for effective glycemic management.

Depending on a patient's particular physiology, a target or set-point glucose level may be established. For example, such a target or set-point glucose level may be defined based, at least in part, on guidelines established by the American Diabetes Association (ADA) and/or clinical judgment of a patient's physician. Here, for example, the ADA has recommended a pre-prandial blood glucose concentration of between 80-130 mg/dl, which is in the normal glycemic range. Alternatively, target or set-point glucose level may be fixed at 120 mg/dl, for example. In yet another alternative, a target or set-point blood glucose concentration may vary over time depending on particular patient conditions. It should be understood, however, that these are merely examples of a target or set-point blood glucose concentration, and claimed subject matter is not limited in this respect.

While techniques for establishing target level or target range for a patient's blood glucose concentration may consider immediate risks of a patient being in either a hypoglycemic or hyperglycemic state, these techniques typically do not consider longer-term effects of a patient being in a hypoglycemic or hyperglycemic state. As mentioned above, a concentration of hemoglobin $A_{1c}$ is typically used as a metric for glycemic health. However, concentration of hemoglobin $A_{1c}$ in a patient is correlated with central tendency (e.g., average) blood glucose concentration and not a statistical dispersion of blood glucose concentration (standard deviation). Concentration of hemoglobin $A_{1c}$ in a patient does not quantify an extent of exposure to glycemic variation (hypoglycemia and hyperglycemia). Other indicators indicative of or correlated with hypoglycemic or hyperglycemic conditions may include, for example, J-index, glycemic risk assessment diabetes equation (GRADE), M-value (e.g., using 100 mg/dl blood glucose concentration as an ideal), versions of the index of glycemic control (e.g., denoted in specific examples as $IGC_1$ and $IGC_2$ herein), coefficient of variation (CV), Kovatchev's low/high blood glucose index (LBGI, HBGI) and total risk index (RI=LBGI+HBGI), % Hypo (e.g., <70 mg/dl), % Hyper (e.g., >140 mg/dl), AUC below 70 mg/dl, AUC above 140 mg/dl, total $AUC_{hypo}$, $AUC_{hyper}$, AUC), interquartile range, and Cameron et al.'s loss function. One or more of these metrics may be applied to a closed-loop glycemic management system as shown in Fraser Cameron, B. Wayne Bequette, Darrell M. Wilson, Bruce A. Buckingham, Hyunjin Lee, and Günter Niemeyer "A Closed-Loop Artificial Pancreas Based on Risk Management," Journal of Diabetes Science and Technology, Volume 5, Issue 2, March 2011. From a virtual population of 10,000 patients, a distribution of 4,000 patient-months of data was collected, a table of Spearman's rank correlation coefficients was created as shown in FIG. 1.

As can be observed, some metrics are strongly correlated with hyperglycemia, including mean blood glucose concentration and $A_{1c}$. Mean blood glucose concentration and $A_{1c}$ metrics are also shown to be negatively correlated with hypoglycemia. Accordingly, use of such metrics to assess glycemic control in an insulin infusion therapy may lead to a tendency toward increased hypoglycemia and/or decreased hyperglycemia. Other metrics are strongly correlated with hypoglycemia and negatively correlated with hyperglycemia. As discussed below in a particular implementation, application of a log square cost function to a blood glucose concentration profile may lead to an insulin therapy providing an improved balance of the immediate risks of hypoglycemia and long-term risks of hyperglycemia.

In one aspect, particular embodiments described herein are directed to techniques for computing a metric enabling an improved control of insulin infusion so as to balance short-term risks and long-term risks associated with particular insulin therapies. In one particular embodiment, a technique for computing such a metric may comprise: characterizing a profile of a patient's blood glucose concentration; applying one or more cost or loss functions to the blood glucose concentration profile to provide a unidimensional value representative of glycemic health of the patient; and affecting a therapy applied to said patient based, at least in part, on the unidimensional value. In a particular embodiment, recognizing that a patient's blood glucose concentration may be roughly statistically distributed according to a lognormal distribution, a cost or loss function for application to a blood glucose concentration may be derived according to a log-square metric.

In one aspect, a unidimensional metric J may be computed as a convolution of a function representing a profile of a patient's blood glucose concentration with a cost or loss function to represent a patient's glycemic health in expression (1) as follows:

$$J=\int_{-\infty}^{\infty} g(x)f(x)dx, \qquad (1)$$

where:
x is a patient's blood glucose concentration;
f(x) is a function representing a profile of the patient's blood glucose concentration; and
g(x) is cost or loss function associated with the patient's blood glucose concentration being at level x.

It should be understood that expression (1) provides merely a single mathematical example of how a blood glucose concentration profile may be convolved with a loss or cost function for computing a unidimensional metric and that other implementations (e.g., in a special purpose computing apparatus programmed with instructions) may be employed without deviating from claimed subject matter.

Here, a unidimensional metric J may enable convenient assessment of a patient's health, and may allow for determination of an insulin infusion therapy that balances short-term and long-term risks of hypoglycemia and hyperglycemia. Here, a unidimensional metric may comprise a single value having a magnitude on a particular scale or range of values, such as a numerical value on a particular scale or range of numerical values. In one particular example, a unidimensional metric may be expressed as a percentage, a value normalized to a range between 0.0 and 1.0, etc. In a particular implementation, a value of J is an indication of glycemic health where a low value represents relatively good or normal glycemic health while a higher value represents poorer glycemic health. In particular implementations, f(x) may represent a patient's blood glucose profile over a longer time period (e.g., a month or longer) or just a few hours.

In one particular implementation, a f(x) may comprise a probability density function of a patient's blood glucose concentration which is determined or estimated using any one of several techniques. In particular example, a probability density function of patient's blood glucose concentration may be constructed from a histogram of blood glucose measurements taken over time using, for example, metered blood glucose reference samples or measurements obtained from a blood glucose sensor in a continuous blood glucose monitoring system. Alternatively, a probability density function of patient's blood glucose concentration may be modeled using any one of several functions used to model a biological process such as, for example, a normal distribution, lognormal distribution, just to name a couple of examples. Parameters for these models of a probability density function of patient's blood glucose concentration (e.g., mean, standard deviation) may be estimated from past observations of the patient's blood glucose concentration using well known techniques.

In another particular implementation, a patient's blood glucose concentration profile f(x) may represent actual measurements blood glucose concentration (e.g., from metered blood glucose measurements or sensor glucose measurements from a continuous glucose monitoring system) collected over a time period.

Figure 3:
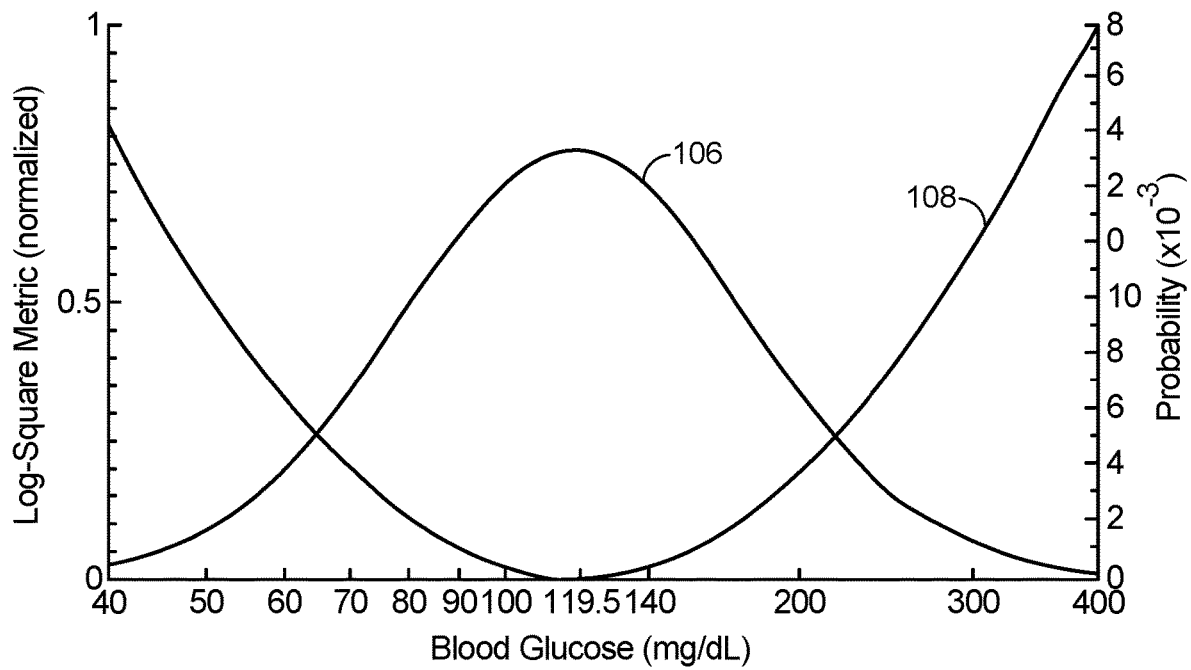
FIG. 3 is a plot of a probability density function on a logarithmic scale laid over a cost or loss function formulated as a log-square metric according to an embodiment.

FIGS. 2 and 3 are example plots of a patient's blood glucose concentration laid over a loss or cost function that may be used to compute unidimensional metric J in particular embodiments. In this particular example, FIG. 2, represents the patient's blood glucose concentration profile as a probability density function in plot 102. Plot 104 represents a quadratic loss or cost function. Here, plots 102 and 104 are shown in a linear domain. Plot 102 is indicative of a skewed probability density function which is not normal, and plot 104, if applied as g(x) as shown above in relation (1), gives significantly more weight to hyperglycemia in computing metric J than it does to hypoglycemia. Alternatively, as illustrated in FIG. 3, plot 106 may represent a patient's blood glucose concentration as a lognormal probability density function. Plot 108, representing a quadratic loss or cost function, may be applied against the blood glucose concentration profile of plot 106.

To account for a skewed blood glucose concentration profile (e.g., represented as a skewed probability distribution of a patient's blood glucose concentration approaching a lognormal distribution as illustrated in FIGS. 2 and 3,), a loss or cost function g(x) to be used in computing J in relation (1) may comprise a log-square metric form shown in expression (2) as follows:

$$g(x) = \left[\log\left(\frac{x}{G_c}\right)\right]^2, \quad (2)$$

Where $G_c$ is a parameter that determines a local minimum or center of a curve in a linear scaled domain.

In a particular implementation, $G_c$ may be selected to according to an optimization to balance Spearman rank coefficients with three hypoglycemic-biased metrics (% Hypo, LBGI and $AUC_{hypo}$) and three hyperglycemic-biased metrics (mean, % Hyper and HBGI). Using values shown in the particular example of the table shown in FIG. 5, a value of $G_c$ is selected as 120 mg/dl. In other implementations, a value of $G_c$ may be selected to balance different glycemic risks according to different metrics as shown as examples in Table 1 as follows:

TABLE 1

| Metric | Centering Value ($G_c$) | Rank Correlation |
|---|---|---|
| A1c | 20 mg/dl | 99% |
| GRADE | 40 mg/dl | 100% |
| M-Value | 45 mg/dl | 99% |
| Risk Index | 115 mg/dl | 99% |
| Cameron et al. | 115 mg/dl | 100% |
| AUC | 120 mg/dl | 97% |

It should be understood that the particular values for $G_c$ and rank correlation are merely example values presented for the purpose of illustration, and that claimed subject matter is not limited to these particular values. For example, retrospective analysis, health care outcome analysis, clinician subjective assessments, randomized clinical trials, and other sources of data can be leveraged to develop more insight around determining an optimal value for $G_c$ for a patient or group of patients, etc.

Figure 6A:
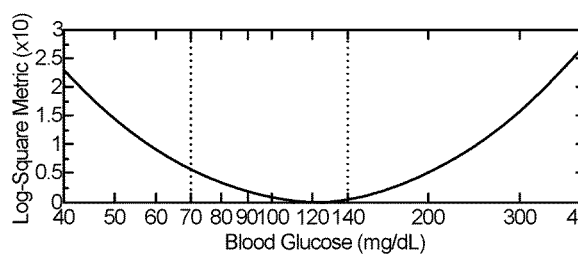
FIGS. 6(a) through 6(d) are plots illustrating application of a loss or cost function to blood glucose concentration profiles of a population of patients according to an embodiment.
Figure 6B:
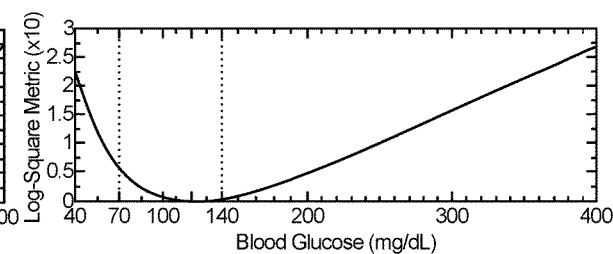
Figure 6C:
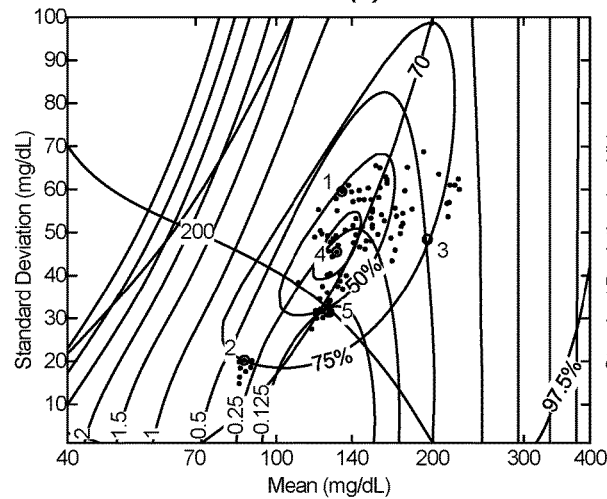
Figure 6D:
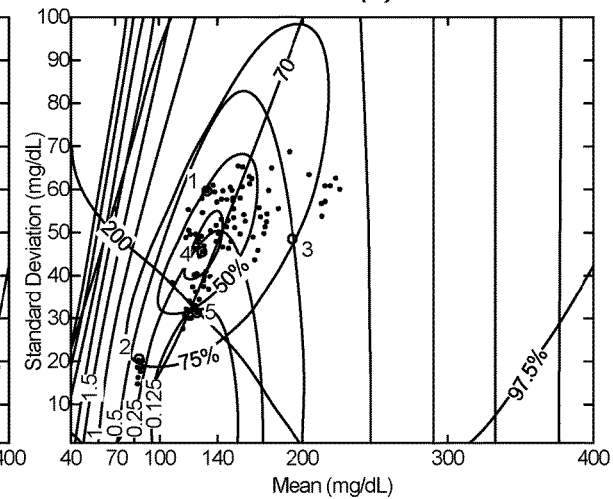

In a recent exercise eight key opinion leaders (KOLs, e.g., physicians and other clinicians) were asked to rank the order of priority in which they would prefer to see a group of five representative patients which having had their blood glucose concentration continuously monitored with blood glucose sensors. The data was shown to them first as the $A_{1c}$ and standard deviation of observed blood glucose concentration (SD). Then they were shown additional data including a probability distribution indicating a duration of time that measured blood glucose concentration remained below 70 mg/dl, between 70 and 140 mg/dl, and above 140 mg/dl. Finally, the KOLs where shown time series data for seven days of blood glucose sensor use for each patient. FIGS. 6(c) and 6(d) show a representative population overlaid on quant plots for application of cost or loss function g(x) using a log-square metric according to expression (1), an isoquant for the 2.5-percentile equal to 70 mg/dl, an isoquant for the 97.5-percentile equal to 200 mg/dl, and contours for population distribution percentiles (25, 50, 75, and 97.5%). KOL rankings correlated well with the log-square metric (Spearman's rank correlation of 0.7). KOL rankings also indicated a bias to treat hypoglycemia first, giving a patient with a median glucose of almost 200 mg/dl the third place instead of the first place as a log-square ranking may indicate. The KOL ranking may reflect an urgency to treat the immediate threat of hypoglycemia, and not necessarily address the quality of glycemic control. Sustained hyperglycemia as exhibited by subject 3 in the KOL ranking indicates poor glycemic control (possibly leading to long-term health risks), but it does not imply an immediate threat to the patient's life (as with hypoglycemia).

Other alternative cost or loss functions applicable for g(x) in relation (1) are shown in the table of FIG. 4. It should be understood, however, that these are merely examples of functions that may provide a cost or loss function for application to a profile of a patient's blood glucose concentration in determining a metric representative of glycemic health, and claimed subject matter is not limited in this respect.

Figure 7:
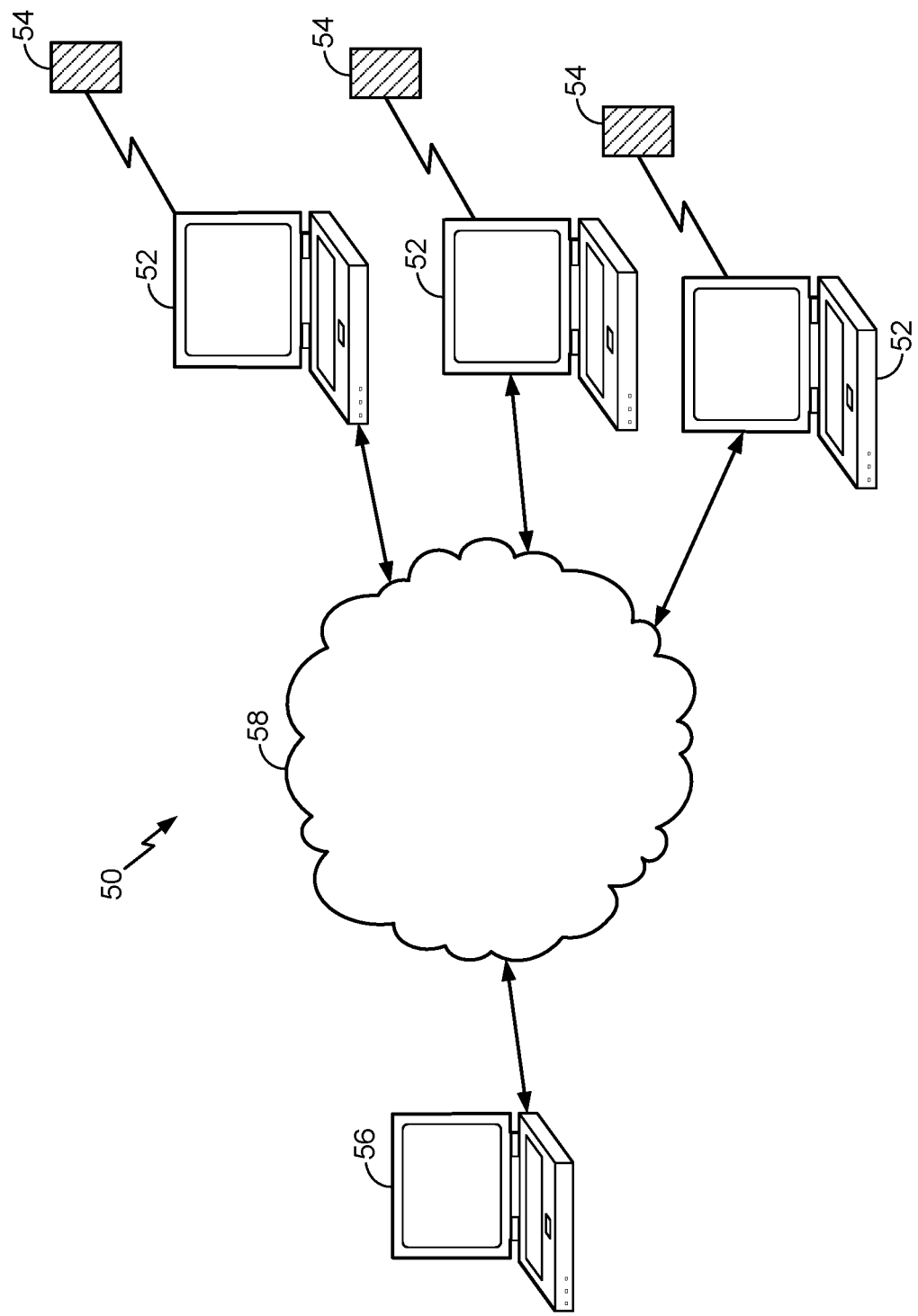
FIG. 7 is a schematic diagram of a system for managing the glycemic health of multiple patients according to an embodiment.

FIG. 7 is a schematic diagram of a system 50 comprising a computing environment according to an embodiment for use in determining and applying a unidimensional metric for indicating glycemic health. Computing platforms 52 may be communicatively coupled to computing platform 56 through network 58. Computing platforms 52 and 56 may have communication interface components to facilitate communication with other devices through network 58 including, for example, modems network adapters and/or the like. Network 58 may comprise any one of several combinations of wired and wireless communication infrastructure including, for example, wired and wireless wide area network infrastructure and/or local area network infrastructure. In a particular implementation, network 58 may provide Internet protocol infrastructure to facilitate communication between computing platform 56 and computing platforms 52 in TCP/IP sessions, HTML, XML or other web service paradigms, for example.

Computing platforms 52 and 56 may comprise processors, memory, input/output devices, display devices, etc., to enable or support applications. For example, a memory may store instructions that are executable by a processor to perform one or more functions, tasks, processes, etc. In particular implementations, computing platforms 52 and 56 may comprise any one of several types of computing devices such as, for example, a server, personal computing, notebook computer, cell phone, smart phone, just to provide a few examples. Computing platforms 52 and 56 may comprise a graphical user interface (GUI) that facilitates user interaction with applications.

In a particular implementation, computing platforms 52 may be communicatively coupled (e.g., wired or wirelessly) to blood glucose monitoring device 54 to receive measurements of a patient's blood glucose concentration. Blood glucose monitoring device 54 may comprise a blood glucose meter capable of receiving blood glucose samples (e.g., from test strips). In another embodiment, blood glucose monitoring device 54 may comprise a blood glucose sensor and monitor for providing continuous blood glucose concentration measurements from processing signals from a blood glucose sensor as described below in a particular implementation with reference to FIGS. 8 through 11.

Computing platforms 52 may be coupled to corresponding blood glucose monitoring devices 54 using a wired or wireless link such as, for example, a universal serial bus, Bluetooth link, ultra wideband link, IEEE Std. 802.11 link, just to provide a few examples. In one example, a monitoring device 54 may comprise a memory (not shown) to store a history of blood glucose concentration measurements to be downloaded to a computing platform 52. Alternatively, a blood glucose monitoring device 54 may forward blood glucose concentration measurements to a computing platform 52 as such blood glucose measurements are received in real-time.

In one implementation, system 50 may be located in a hospital environment where computing platforms 52 are co-located with patients at different locations communicate with a central computing platform 56 to centrally collect and process patient data. In another implementation, system 50 may be more geographically distributed in that central computing platform 50 may be located in doctor's office or medical clinic while computing platforms 52 are located in patients' homes. Here, a unidimensional metric J may be computed for each patient to assess the patient's glycemic health. In one implementation, the centrally computed unidimensional metrics may allow for tailoring insulin therapies to the particular needs of the patients. In another implementation, the centrally computed unidimensional metrics may be incorporating in a process for triaging patients so that patients having the most severe conditions are treated with a priority over patients with least severe conditions. For example, patients with a higher computed unidimensional metric J may be treated with priority over patients with a lower computed unidimensional metric J. In another implementation, computing platforms 52 may have sufficient software program resources to compute a unidimensional metric J based, at least in part, on blood glucose measurements collected for a single patient at a blood glucose monitoring device 54 and without interaction with a central computing platform 56.

In another embodiment, unidimensional metric J may be computed using a brief history of blood glucose measurements (e.g., over a three hour period) to obtain a snapshot of a patient's glycemic health. Here, a patient's glycemic health may be evaluated for different recurring conditions, time of day, time of week, etc. For example, a diabetic patient's dietary or exercise habits during typical week days may be different from the patient's dietary or exercise habits on the weekend, affecting the patient's glycemic health. It may be of interest, for example, to assess the patient's glycemic health on particular periodically repeating periods such as, for example, time of day (e.g., morning before first meal, afternoon following lunch time, in the evening before or after bedtime, etc.), day of week (e.g., Mondays following a weekend of altered exercise and dietary habits), time of month, time of year (e.g., during or following the holiday season), just to provide a few example of periodically repeating periods.

In one particular example, a unidimensional metric J to indicate glycemic health over a periodically repeating period may be computed based, at least in part, on a profile f(x) based, at least in part, on blood glucose concentration measurements as discussed above (e.g., either from metered blood glucose samples or from a blood glucose sensor in a continuous blood glucose monitoring system) collected over the periodically repeating period. For computing unidimensional metric J for Mondays, in a particular example, a patient's blood glucose concentration profile f(x) may comprise blood glucose concentration measurements collected over the 24-hour period on Mondays over multiple weeks. Similarly, for computing unidimensional metric J for a time of day (e.g., from 9 am to noon), a patient's blood glucose concentration profile f(x) may comprise blood glucose concentration measurements collected during this particular time over multiple days. Similarly, for computing unidimensional metric J for a time of year (e.g., holiday period from late November to early January), a patient's blood glucose concentration profile f(x) may comprise blood glucose concentration measurements collected during this time of the year over multiple years. Here, a patient's blood glucose concentration profile may be determined from blood glucose concentration measurements or observations limited to such measurements or observations obtained during the particular periodically repeating period of interest.

In one particular implementation, a blood glucose concentration profile f(x) characterizing blood glucose concentration for use in computing a metric may be expressed as follows:

f(x)=f(x|ξ), where ξ represents a particular recurring condition or period of interest.

Here, $f(x|\xi)$ may represent a profile of a patient's blood glucose concentration profile based only on observations of the patient's blood glucose concentration obtained during recurring condition period ξ. For example, as discussed above, f(x|ξ) may comprise an estimated probability distribution or a histogram derived from observations of the patient's blood glucose concentration obtained during recurring condition period ξ, or merely measurements of the patient's blood glucose concentration obtained during recurring condition period ξ.

As discussed above, unidimensional metric J may be computed according to a cost or loss function g(x) so as to indicate a patient's glycemic health based, at least in part, on factors or risks indicative of hypoglycemia or hyperglycemia. Application of a particular cost or loss function g(x) as a log-square metric as shown in expression (2) may quantify effects of a blood glucose concentration being in a hypoglycemic or hyperglycemic region (e.g., being below or above $G_c$). While providing a convenient indicator of a patient's glycemic health, application of the log-square metric shown in expression (2) as loss or cost function g(x) in expression (1) to compute J, by itself, may not indicate whether a relatively high value for J (indicating a diminished glycemic health, for example) is brought about by hypoglycemia, hyperglycemia, or a mixture of hypoglycemic and hyperglycemic.

In one implementation, a "one sided" loss or cost function may be selectively applied for isolating and quantifying effects of hyperglycemia to the exclusion of effects of hypoglycemia, or quantifying effects of hypoglycemia to the exclusion of effects of hyperglycemia. Here, application of g(x) according to expression (3) below may isolate and quantify effects of hyperglycemia to the exclusion of effects of hypoglycemia:

$$g(x) = \left[\log\left(\frac{x}{G_c}\right)\right]^2, \text{ for } x \geq G_c \quad (3)$$
$$= 0, \text{ for } x < G_c.$$

By convolving a patient's blood glucose concentration profile f(x) in expression (1) to compute metric J with g(x) as provided in a one-sided loss or cost function according to either expression (3), we can compute and quantify the effect of hyperglycemia in isolation. Similarly, application of g(x) according to expression (4) below may isolate and quantify effects of hypoglycemia to the exclusion of effects of hyperglycemia:

$$g(x) = \left[\log\left(\frac{x}{G_c}\right)\right]^2, \text{ for } x \leq G_c \quad (4)$$
$$= 0, \text{ for } x > G_c.$$

By convolving a patient's blood glucose concentration profile f(x) in expression (1) to compute metric J with g(x) as provided in a one-sided loss or cost function according to either expression (4), we can compute and quantify the effect of hypoglycemia in isolation. While the particular examples of a one-sided loss or cost function in expressions (3) and (4) employ a log-square metric loss or cost function, it should be understood that such an application of a log-square metric is presented merely as an example, and that a one-sided loss or cost function may be derived from different expressions without deviating from claimed subject matter.

As discussed above, computation of unidimensional metric J may facilitate evaluation of a patient's glycemic health for different recurring conditions, time of day, time of week, etc. While convolving a patient's blood glucose concentration profile f(x) with cost or loss function g(x) according to relation (2) may identify recurring conditions, time of day, time of week, etc., where glycemic health is affected (e.g., as indicated by a high number for J over a period in question), this computation of J may not be indicative of either hyperglycemia or hypoglycemia. In one implementation, in periods or conditions under which a computed metric J indicates a decline in glycemic health for a particular blood glucose concentration profile f(x), the particular blood glucose concentration profile f(x) may be convolved again separately with one-sided loss or cost functions g(x) as set forth in expressions (3) and (4). The results of convolutions of f(x) separately with loss or cost functions g(x) as set forth in expressions (3) and (4) may be indicative of the effects of hyperglycemia in isolation and hypoglycemia, respectively.

In another implementation, a particular blood glucose concentration profile f(x) may be convolved separately with loss or cost functions g(x) as set forth in expressions (3) and (4) to provide a bi-dimensional metric indicative of the effects of hyperglycemia and hypoglycemia, separately, in two distinct dimensions. For example, two values $J_{Hyper}$ and $J_{Hypo}$, indicating glycemic health or risk in a hyperglycemia and hypoglycemia dimensions, respectively, may be computed using a log-square metric cost or loss function in expression (5) as follows:

$$J_{Hyper} = \int_{G_c}^{\infty} \left[\log\left(\frac{x}{G_c}\right)\right]^2 f(x)dx, \text{ and} \quad (5)$$
$$J_{Hypo} = \int_{-\infty}^{G_c} \left[\log\left(\frac{x}{G_c}\right)\right]^2 f(x)dx.$$

While expression (5) applies a log-square loss or cost function, it should be understood that other loss or cost functions may be used without deviating from claimed subject matter. Separately identifying effects of hyperglycemic and hypoglycemic conditions contributing to glycemic health according to expression (5) may enable more effective therapies for managing a patient's glycemic health. As discussed above, unidimensional metric J may be computed for a patient's blood glucose concentration profile f(x) over different recurring conditions, times of day, day of week, time of year, etc. Application of a one-sided loss or cost function g(x) (e.g., as in expression (3) or (4)) in computing J or application of a bi-dimensional metric may allow for further identification of how glycemic health is being effected in these different recurring conditions, times of day, day of week, time of year, etc. (e.g., by hypoglycemia or hypoglycemia). By identifying a patient as experiencing either hyperglycemia or hypoglycemia for a particular recurring condition, time of day, day of week, time of year, etc, a patient's therapy or behavior may be altered to address the particular hyperglycemic or hypoglycemic state. To counteract a particular hyperglycemic or hypoglycemic state for a particular recurring condition, for example, a patient may alter diet, exercise or insulin therapy (e.g., insulin infusion basal rate), or reduce stress, just to name a few examples.

In a particular implementation, a bi-dimensional metric may be used to adjust a patient's target blood glucose concentration level or range. For example, as described in U.S. patent application Ser. No. 12/820,944, filed on Jun. 22, 2010 and assigned to the assignee of claimed subject matter, a closed-loop blood glucose monitoring and insulin deliver system may establish a target blood glucose concentration level or target range. This target range may be adjusted upward, for example, if the patient is tending to be hypoglycemic for a particular recurring period, or adjusted downward if the patient is tending to be hyperglycemic. Such an adjustment of a target glucose level or target range may allow for a better balance of the immediate risks of a hypoglycemic condition with the longer-term risks of a hyperglycemic condition.

Figure 8:
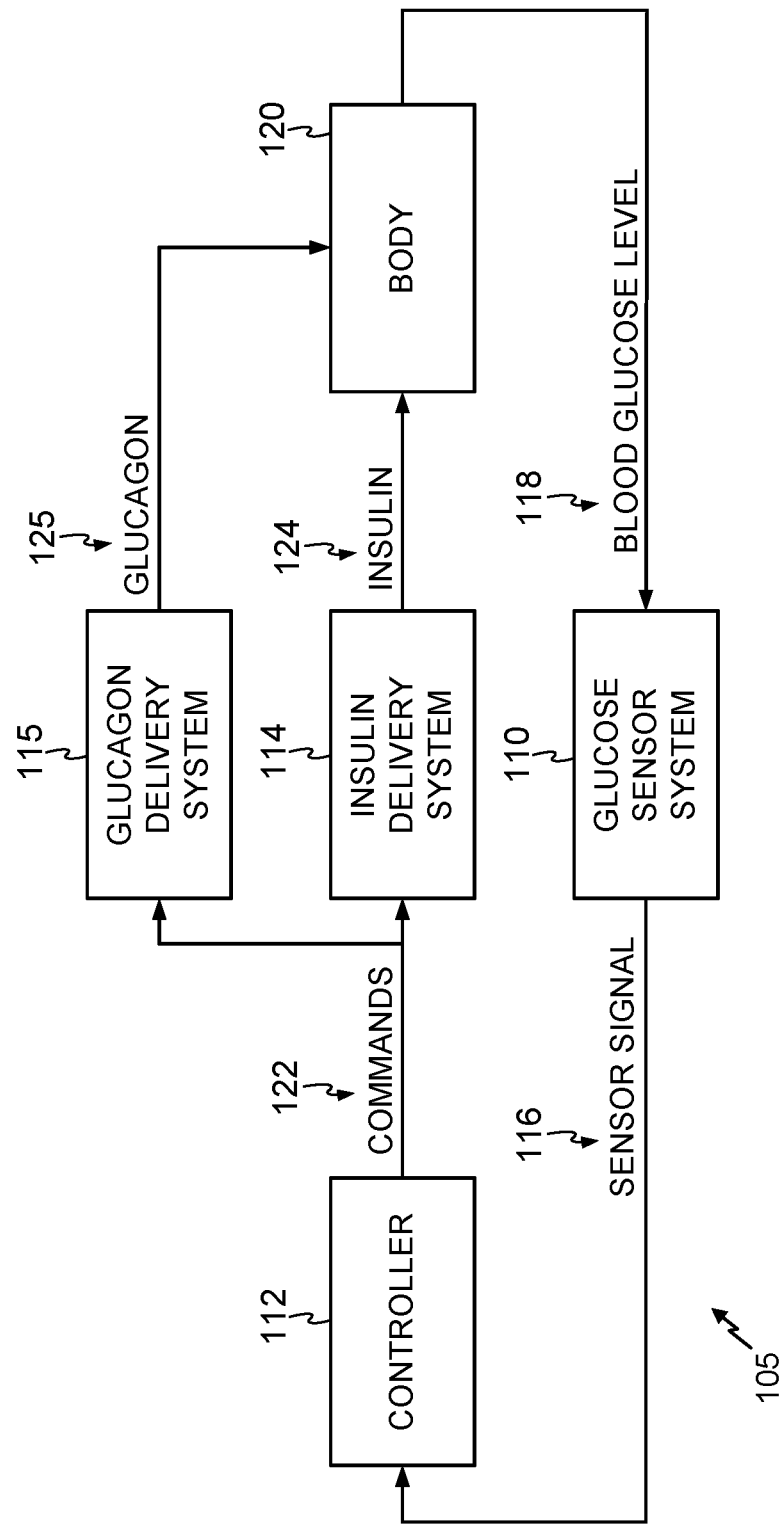
FIG. 8 is a schematic diagram of an example closed loop glucose control system in accordance with an embodiment.

FIG. 8 is a block diagram of an example closed loop glucose control system 105 in accordance with an embodiment. Particular embodiments may include a glucose sensor system 110, a controller 112, an insulin delivery system 114, and a glucagon delivery system 115, etc. as shown in FIG. 8. In certain example embodiments, glucose sensor system 110 may generate a sensor signal 116 representative of blood glucose levels 118 in body 120, and glucose sensor system 110 may provide sensor signal 116 to controller 112. Controller 112 may receive sensor signal 116 and generate commands 122 that are communicated at least to insulin delivery system 114 and/or glucagon delivery system 115. Insulin delivery system 114 may receive commands 122 and infuse insulin 124 into body 120 in response to commands 122. Likewise, glucagon delivery system 115 may receive commands 122 from controller 112 and infuse glucagon 125 into body 120 in response to commands 122.

Glucose sensor system 110 may include, by way of example but not limitation, a glucose sensor; sensor electrical components to provide power to a glucose sensor and to generate sensor signal 116; a sensor communication system to carry sensor signal 116 to controller 112; a sensor system housing for holding, covering, and/or containing electrical components and a sensor communication system; any combination thereof, and so forth.

Controller 112 may include, by way of example but not limitation, electrical components, other hardware, firmware, and/or software, etc. to generate commands 122 for insulin delivery system 114 and/or glucagon delivery system 115 based at least partly on sensor signal 116. Controller 112 may also include a controller communication system to receive sensor signal 116 and/or to provide commands 122 to insulin delivery system 114 and/or glucagon delivery system 115. In particular example implementations, controller 112 may include a user interface and/or operator interface (not shown) comprising a data input device and/or a data output device. Such a data output device may, for example, generate signals to initiate an alarm and/or include a display or printer for showing a status of controller 112 and/or a patient's vital indicators, monitored historical data, combinations thereof, and so forth. Such a data input device may comprise dials, buttons, pointing devices, manual switches, alphanumeric keys, a touch-sensitive display, combinations thereof, and/or the like for receiving user and/or operator inputs. It should be understood, however, that these are merely examples of input and output devices that may be a part of an operator and/or user interface and that claimed subject matter is not limited in these respects.

Insulin delivery system 114 may include an infusion device and/or an infusion tube to infuse insulin 124 into body 120. Similarly, glucagon delivery system 115 may include an infusion device and/or an infusion tube to infuse glucagon 125 into body 120. In alternative embodiments, insulin 124 and glucagon 125 may be infused into body 120 using a shared infusion tube. In other alternative embodiments, insulin 124 and/or glucagon 125 may be infused using an intravenous system for providing fluids to a patient (e.g., in a hospital or other medical environment). While an intravenous system is employed, glucose may be infused directly into a bloodstream of a body instead of or in addition to infusing glucagon into interstitial tissue. It should also be understood that certain example embodiments for closed loop glucose control system 105 may include an insulin delivery system 114 without a glucagon delivery system 115 (or vice versa).

In particular example embodiments, an infusion device (not explicitly identified in FIG. 8) may include electrical components to activate an infusion motor according to commands 122; an infusion communication system to receive commands 122 from controller 112; an infusion device housing (not shown) to hold, cover, and/or contain the infusion device; any combination thereof; and so forth.

In particular example embodiments, controller 112 may be housed in an infusion device housing, and an infusion communication system may comprise an electrical trace or a wire that carries commands 122 from controller 112 to an infusion device. In alternative embodiments, controller 112 may be housed in a sensor system housing, and a sensor communication system may comprise an electrical trace or a wire that carries sensor signal 116 from sensor electrical components to controller electrical components. In other alternative embodiments, controller 112 may have its own housing or may be included in a supplemental device. In yet other alternative embodiments, controller 112 may be co-located with an infusion device and a sensor system within one shared housing. In further alternative embodiments, a sensor, a controller, and/or infusion communication systems may utilize a cable; a wire; a fiber optic line; RF, IR, or ultrasonic transmitters and receivers; combinations thereof; and/or the like instead of electrical traces, just to name a few examples.

Figure 9:
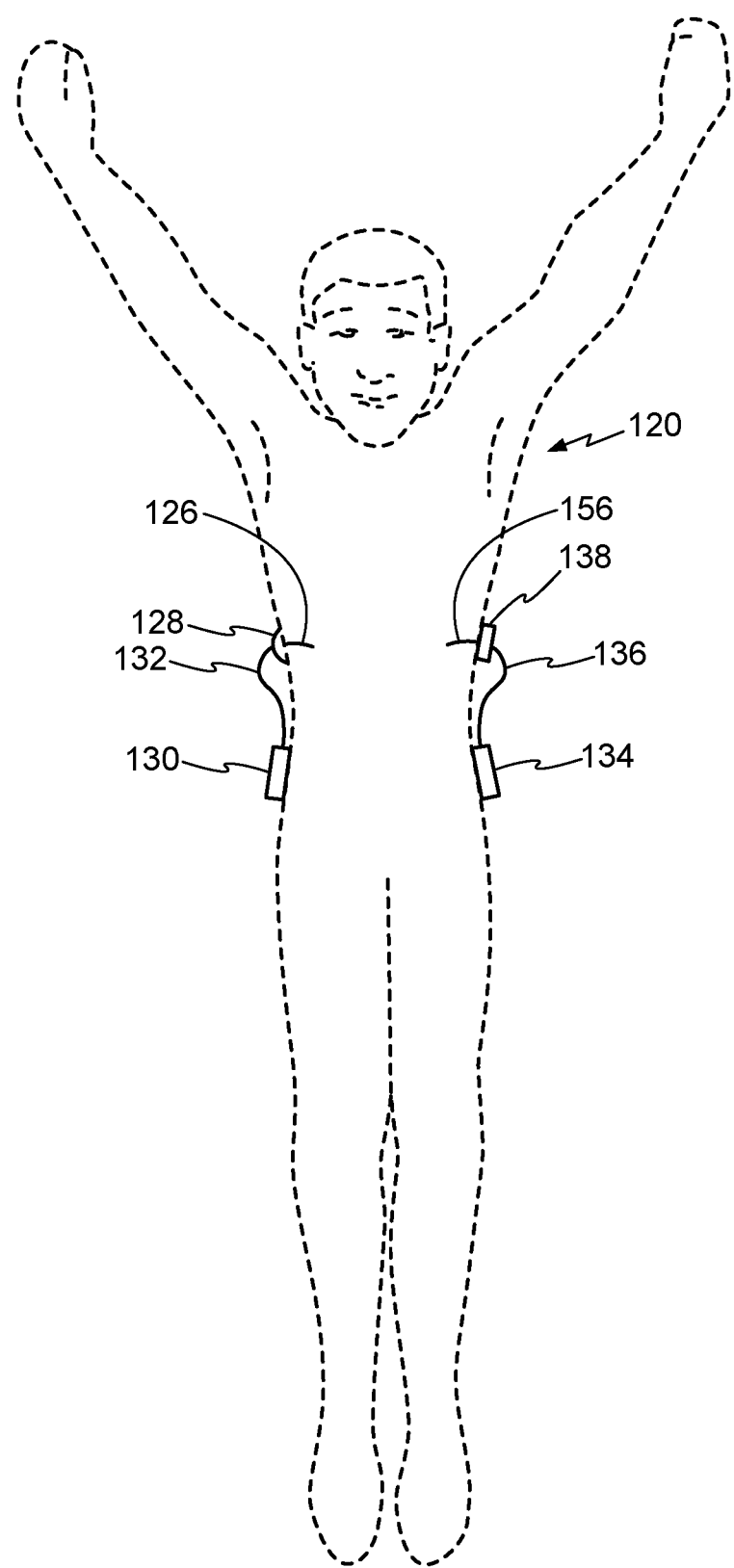
FIG. 9 is a front view of example closed loop hardware located on a body in accordance with an embodiment.
Figure 10C:
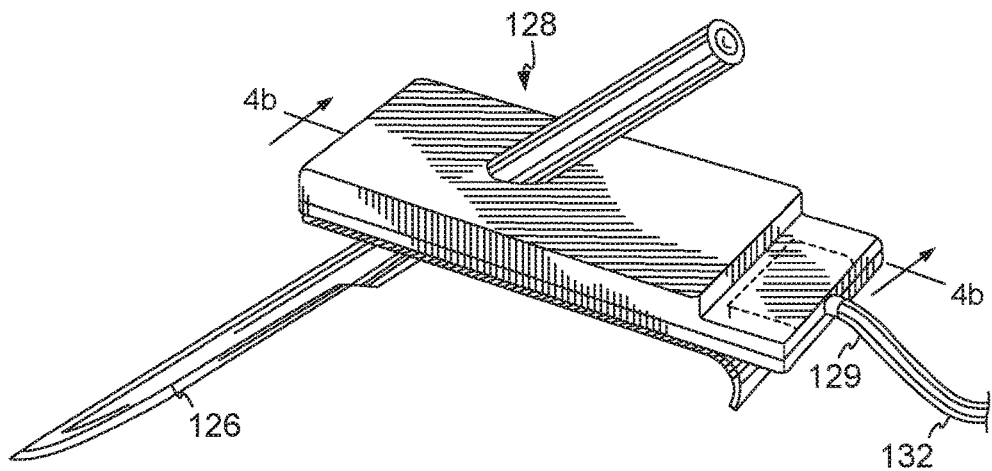
FIG. 10(c) is a perspective view of an example sensor set for a glucose sensor system of FIG. 10(a) for use in accordance with an embodiment.
Figure 10D:
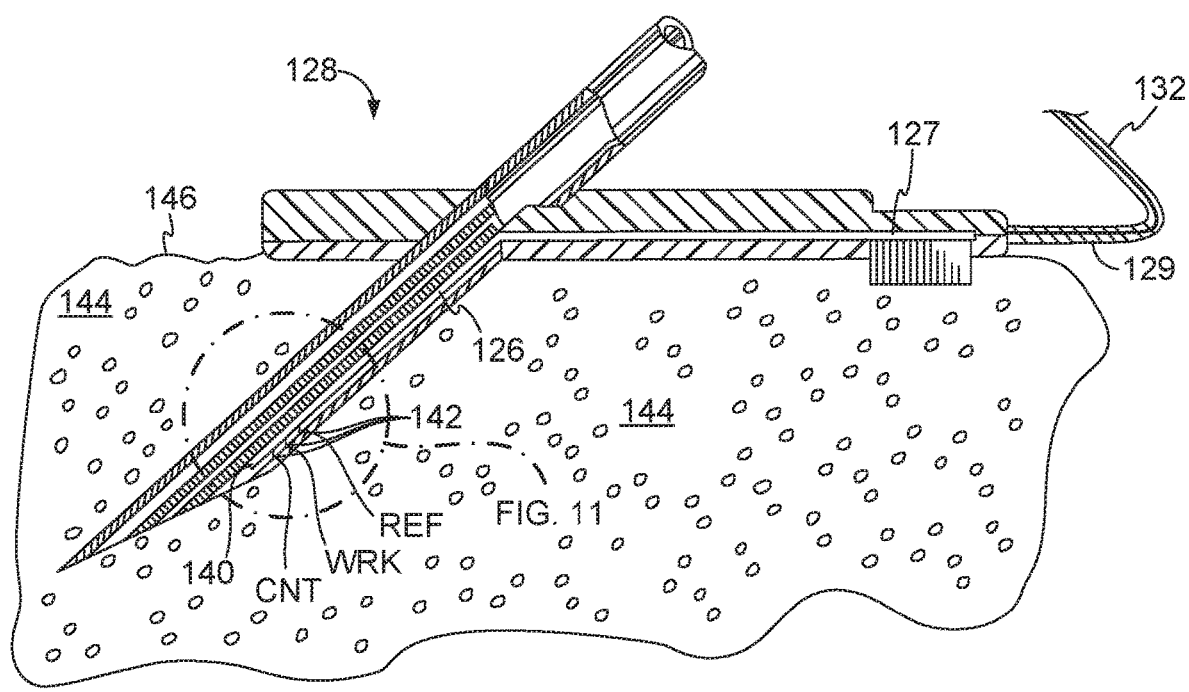
FIG. 10(d) is a side cross-sectional view of a sensor set of FIG. 10(c) for an embodiment.
Figure 11:
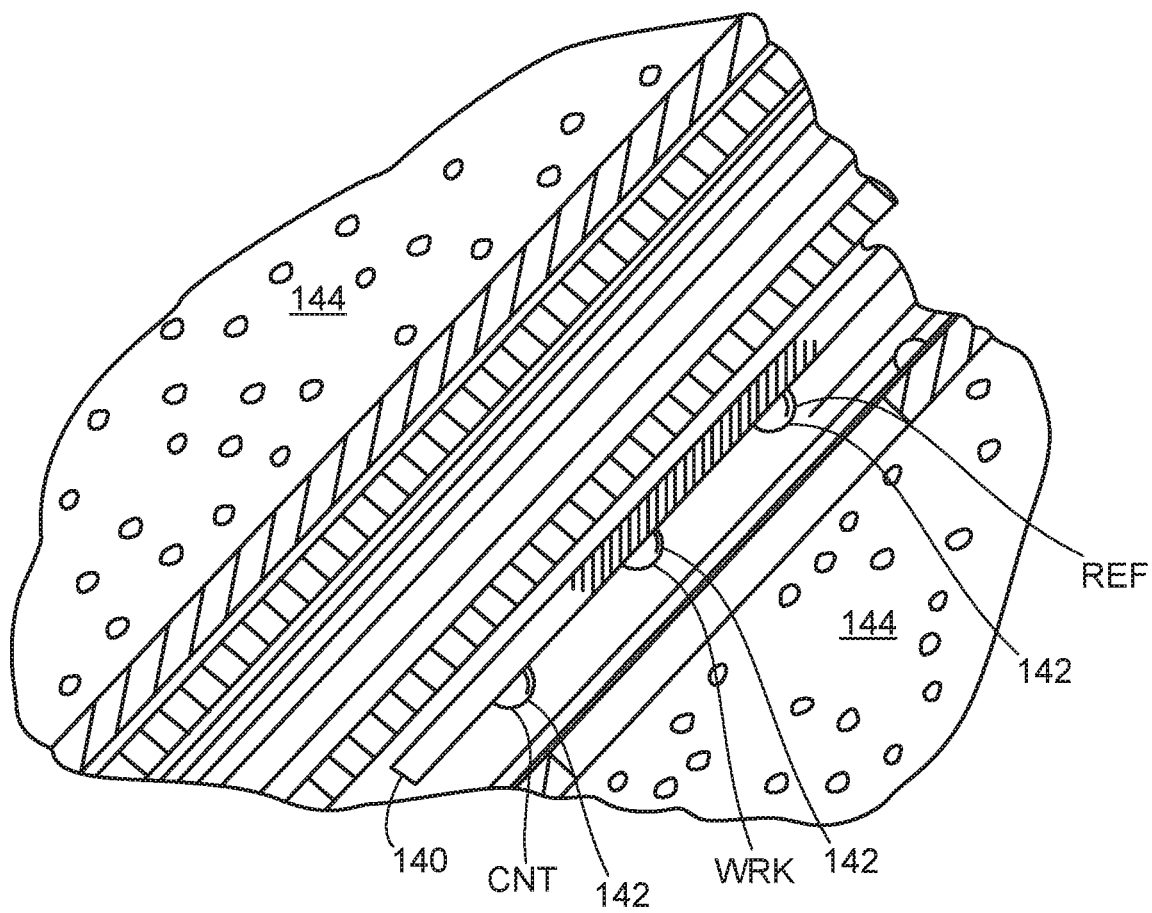
FIG. 11 is a cross sectional view of an example sensing end of a sensor set of FIG. 10(d) for use in accordance with an embodiment.
Figure 12:
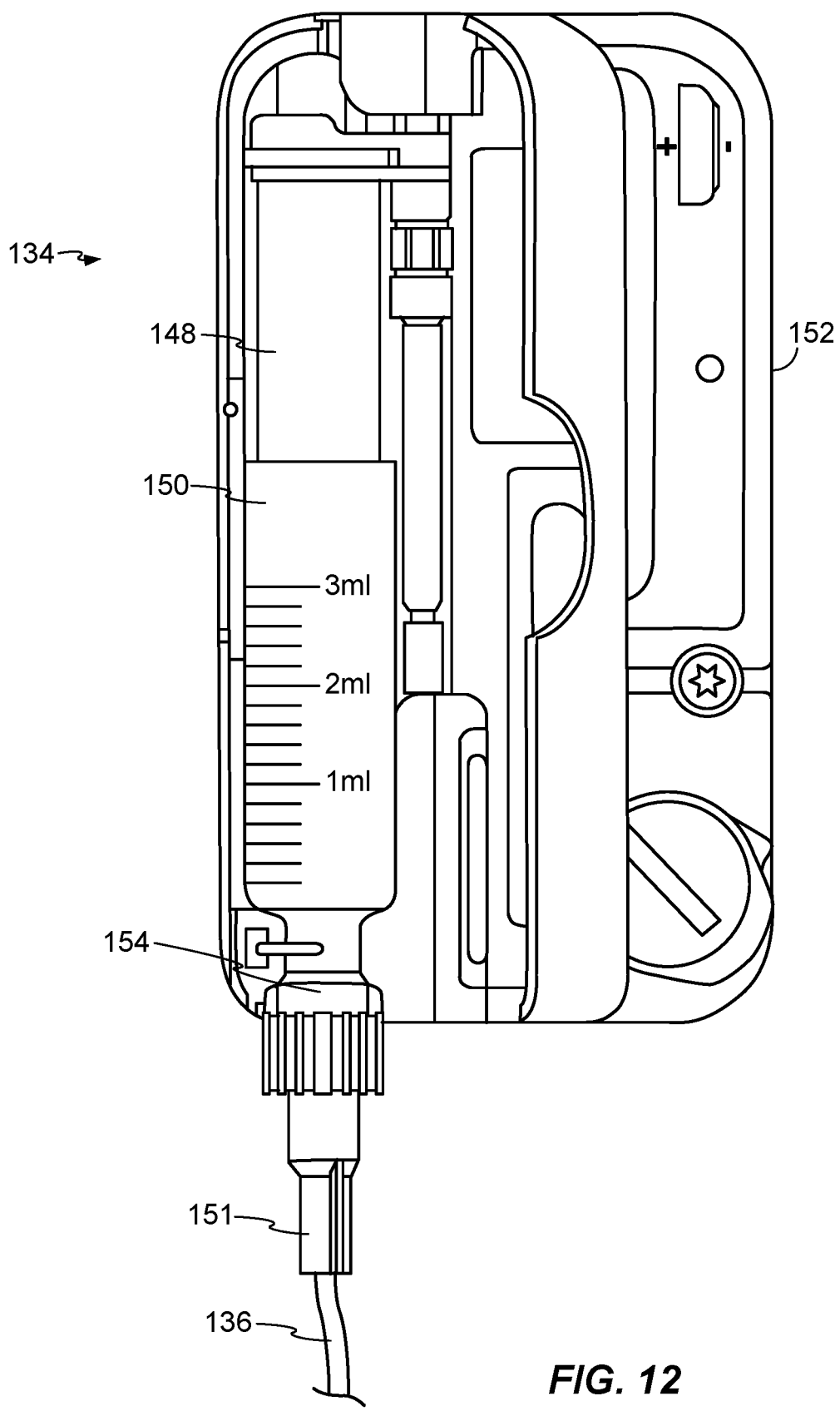
FIG. 12 is a top view of an example infusion device with a reservoir door in an open position, for use according to an embodiment.
Figure 13:
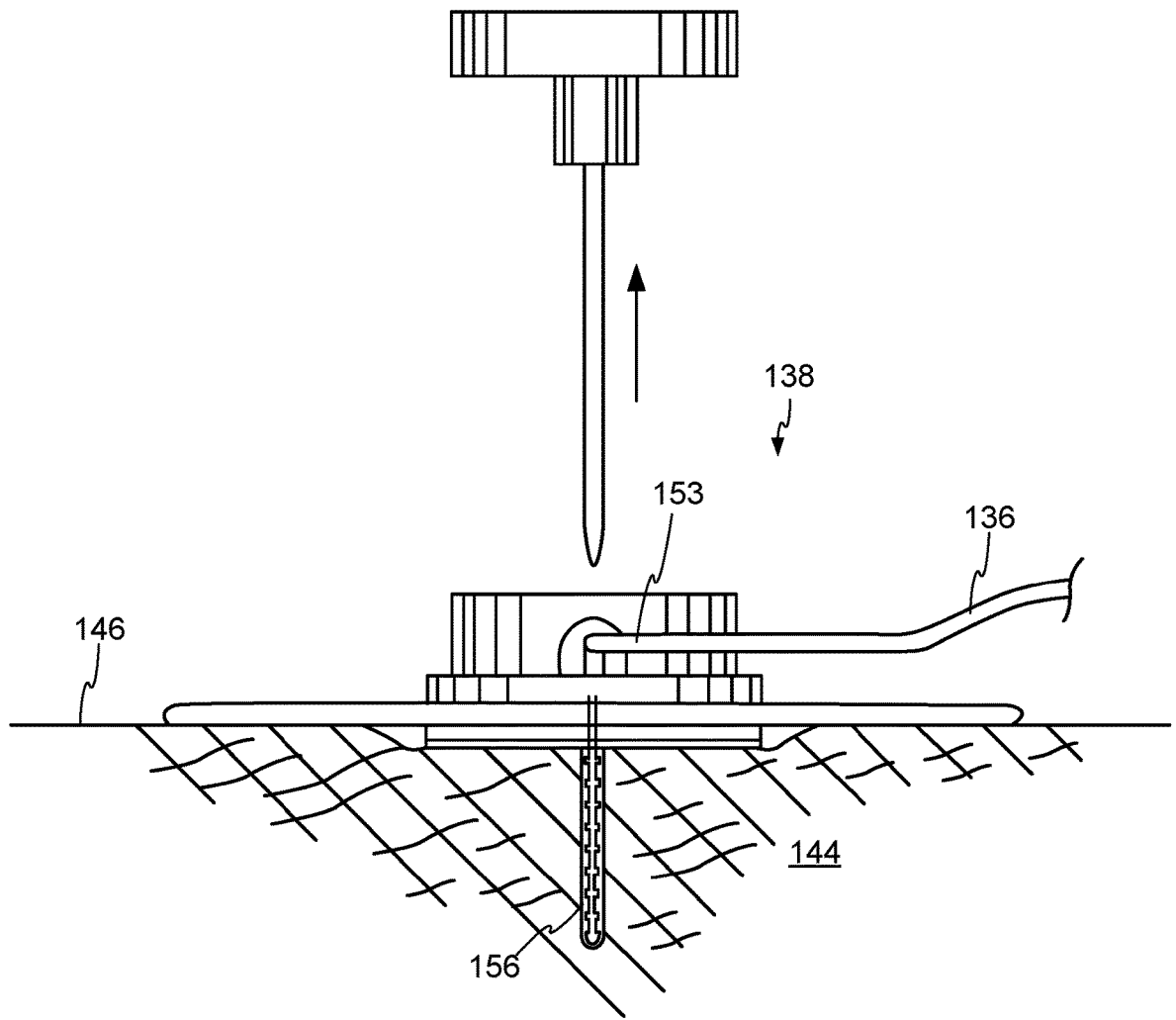
FIG. 13 is a side view of an example infusion set with an insertion needle pulled out, for use according to an embodiment.

FIGS. 9 through 13 illustrate example glucose control systems in accordance with certain embodiments. FIG. 9 is a front view of example closed loop hardware located on a body in accordance with certain embodiments. FIGS. 10(a)-10(d) and 11 show different views and portions of an example glucose sensor system for use in accordance with certain embodiments. FIG. 12 is a top view of an example infusion device with a reservoir door in an open position in accordance with certain embodiments. FIG. 13 is a side view of an example infusion set with an insertion needle pulled out in accordance with certain embodiments.

Particular example embodiments may include a sensor 126, a sensor set 128, a telemetered characteristic monitor 130, a sensor cable 132, an infusion device 134, an infusion tube 136, and an infusion set 138, any or all of which may be worn on a body 120 of a user or patient, as shown in FIG. 9. As shown in FIGS. 10(a) and 10(b), telemetered characteristic monitor 130 may include a monitor housing 131 that supports a printed circuit board 133, battery or batteries 135, antenna (not shown), a sensor cable connector (not shown), and so forth. A sensing end 140 of sensor 126 may have exposed electrodes 142 that may be inserted through skin 146 into a subcutaneous tissue 144 of a user's body 120, as shown in FIGS. 10(d) and 11. Electrodes 142 may be in contact with interstitial fluid (ISF) that is usually present throughout subcutaneous tissue 144.

Sensor 126 may be held in place by sensor set 128, which may be adhesively secured to a user's skin 146, as shown in FIGS. 10(c) and 10(d). Sensor set 128 may provide for a connector end 27 of sensor 26 to connect to a first end 129 of sensor cable 132. A second end 137 of sensor cable 132 may connect to monitor housing 131. Batteries 135 that may be included in monitor housing 131 provide power for sensor 126 and electrical components 139 on printed circuit board 133. Electrical components 139 may sample a current of sensor signal 116 (e.g., of FIG. 8) to provide digital sensor values (Dsig) and store Dsig values in a memory. Digital sensor values Dsig may be periodically transmitted from a memory to controller 112, which may be included in an infusion device.

In a particular implementation, controller 112 may perform additional filtering and processing on values for Dsig to compute continuous sensor blood glucose measurements as described in U.S. patent application Ser. No. 12/345,477, filed on Dec. 29, 2008, and Ser. No. 12/347,716, filed on Dec. 31, 2008, assigned to the assignee of claimed subject matter and incorporated herein by reference. These continuous blood glucose measurements may then be used for determining a patient's blood glucose concentration profile f(x) for use in computing unidimensional metric J as set forth in expression (1) above, for example. For example, these sensor blood glucose measurements may themselves be directly convolved with g(x) to produce J according to relation (1). Alternatively, sensor blood glucose measurements may be used to estimate parameters of a probability density function modeling a patient's blood glucose concentration.

With reference to FIGS. 8, 9 and 12, a controller 112 may process digital sensor values Dsig and generate commands 122 for infusion device 134. Infusion device 134 may respond to commands 122 and actuate a plunger 148 that forces insulin 124 out of a reservoir 150 that is located inside an infusion device 134. Glucose may be infused from a reservoir responsive to commands 122 using a similar and/or analogous device (not shown). In alternative implementations, glucose may be administered to a patient orally.

In particular example embodiments, a connector tip 154 of reservoir 150 may extend through infusion device housing 152, and a first end 151 of infusion tube 136 may be attached to connector tip 154. A second end 153 of infusion tube 136 may connect to infusion set 138 (e.g., of FIGS. 9 and 13). Insulin 124 may be forced through infusion tube 136 into infusion set 138 and into body 116. Infusion set 138 may be adhesively attached to a user's skin 146. As part of infusion set 138, a cannula 156 may extend through skin 146 and terminate in subcutaneous tissue 144 to complete fluid communication between a reservoir 150 and subcutaneous tissue 144 of a user's body 116.

In one implementation, a unidimensional (e.g., J) or bi-dimensional metric (e.g., $J_{Hypo}$ in combination with $J_{Hyper}$) may be used in real-time control of a closed-loop system (e.g., as shown in FIG. 8) to provide insulin and/or glucagon. For example, a controller 112 may compute a control signal on a periodic basis to be used in formulating commands for a pump to infuse insulin and/or glucagon. Here, application of a unidimensional or bi-dimensional metric in formulating real-time commands in a closed loop system may allow for an improved balancing of the immediate risk of hypoglycemia and the long-term risks of hyperglycemia, for example.

In another example implementation, a unidimensional or bi-dimensional metric as discussed above may be used for triggering an alarm for a patient under certain conditions. As discussed above, during particular times of day, days of week, etc. a patient may be likely to encounter greater risks hyperglycemia or hypoglycemia than other times of day, days of week, etc. Under such a condition, an alarm signal may be triggered if a unidimensional or bi-dimensional metric as discussed above exceeds a threshold value. The alarm signal may initiate an audible or visual signal to cue the patient, or automatically initiate a change in therapy provided by a closed-loop system, for example.

In yet another example implementation, a unidimensional or bi-dimensional metric as discussed above may be used for performing optimization studies for the evaluation and design of control algorithms (e.g., control algorithms such as a closed-loop system for providing insulin and/or glucagon based, at least in part, on sensor glucose measurements. Here, a unidimensional or bi-dimensional metric may be conveniently computed over data sets covering large numbers individuals. The different therapies may then be ranked based upon an average value of J, for example.

In example alternative embodiments, as pointed out above, a closed-loop system in particular implementations may be a part of a hospital-based glucose management system. Given that insulin therapy during intensive care has been shown to dramatically improve wound healing and reduce blood stream infections, renal failure, and polyneuropathy mortality, irrespective of whether subjects previously had diabetes (See, e.g., Van den Berghe G. et al. NEJM 345: 1359-67, 2001), particular example implementations may be used in a hospital setting to control a blood glucose level of a patient in intensive care. In such alternative embodiments, because an intravenous (IV) hookup may be implanted into a patient's arm while the patient is in an intensive care setting (e.g., ICU), a closed loop glucose control may be established that piggy-backs off an existing IV connection. Thus, in a hospital or other medical-facility based system, IV catheters that are directly connected to a patient's vascular system for purposes of quickly delivering IV fluids, may also be used to facilitate blood sampling and direct infusion of substances (e.g., insulin, glucose, anticoagulants, etc.) into an intra-vascular space.

Moreover, glucose sensors may be inserted through an IV line to provide, e.g., real-time glucose levels from the blood stream. Therefore, depending on a type of hospital or other medical-facility based system, such alternative embodiments may not necessarily utilize all of the described system components. Examples of components that may be omitted include, but are not limited to, sensor 126, sensor set 128, telemetered characteristic monitor 130, sensor cable 132, infusion tube 136, infusion set 138, and so forth. Instead, standard blood glucose meters and/or vascular glucose sensors, such as those described in co-pending U.S. Patent Application Publication No. 2008/0221509 (U.S. patent application Ser. No. 12/121,647; to Gottlieb, Rebecca et al.; entitled "MULTILUMEN CATHETER"), filed 15 May 2008, may be used to provide blood glucose values to an infusion pump control, and an existing IV connection may be used to administer insulin to an patient. Other alternative embodiments may also include fewer, more, and/or different components than those that are described herein and/or illustrated in the accompanying Drawings.

Controller 112, and computing devices 52 and 56 may comprise one or more processors capable of executing instructions to thereby render controller 112, or computing devices 52 and 56 a special purpose computing device to perform algorithms, functions, methods, etc.; to implement attributes, features, etc.; and so forth that are described herein. Such processor(s) may be realized as microprocessors, digital signal processors (DSPs), application specific integrated circuits (ASICs), programmable logic devices (PLDs), controllers, micro-controllers, a combination thereof, and so forth, just to name a few examples. Alternatively, an article may comprise at least one storage medium (e.g., such as one or more memories) having stored thereon instructions 1706 that are executable by one or more processors.

Unless specifically stated otherwise, as is apparent from the preceding discussion, it is to be appreciated that throughout this specification discussions utilizing terms such as "processing", "computing", "calculating", "determining", "assessing", "estimating", "identifying", "obtaining", "representing", "receiving", "transmitting", "storing", "analyzing", "measuring", "detecting", "controlling", "delaying", "initiating", "providing", "performing", "generating", "altering" and so forth may refer to actions, processes, etc. that may be partially or fully performed by a specific apparatus, such as a special purpose computer, special purpose computing apparatus, a similar special purpose electronic computing device, and so forth, just to name a few examples. In the context of this specification, therefore, a special purpose computer or a similar special purpose electronic computing device may be capable of manipulating or transforming signals, which are typically represented as physical electronic and/or magnetic quantities within memories, registers, or other information storage devices; transmission devices; display devices of a special purpose computer; or similar special purpose electronic computing device; and so forth, just to name a few examples. In particular example embodiments, such a special purpose computer or similar may comprise one or more processors programmed with instructions to perform one or more specific functions. Accordingly, a special purpose computer may refer to a system or a device that includes an ability to process or store data in the form of signals. Further, unless specifically stated otherwise, a process or method as described herein, with reference to flow diagrams or otherwise, may also be executed or controlled, in whole or in part, by a special purpose computer.

It should be understood that aspects described above are examples only and that embodiments may differ there from without departing from claimed subject matter. Also, it should be noted that although aspects of the above systems, methods, apparatuses, devices, processes, etc. have been described in particular orders and in particular arrangements, such specific orders and arrangements are merely examples and claimed subject matter is not limited to the orders and arrangements as described. It should additionally be noted that systems, devices, methods, apparatuses, processes, etc. described herein may be capable of being performed by one or more computing platforms.

In addition, instructions that are adapted to realize methods, processes, etc. that are described herein may be capable of being stored on a storage medium as one or more machine readable instructions. If executed, machine readable instructions may enable a computing platform to perform one or more actions. "Storage medium" as referred to herein may relate to media capable of storing information or instructions which may be operated on, or executed by, one or more machines (e.g., that include at least one processor). For example, a storage medium may comprise one or more storage articles and/or devices for storing machine-readable instructions or information. Such storage articles and/or devices may comprise any one of several media types including, for example, magnetic, optical, semiconductor, a combination thereof, etc. storage media. By way of further example, one or more computing platforms may be adapted to perform one or more processes, methods, etc. in accordance with claimed subject matter, such as methods, processes, etc. that are described herein. However, these are merely examples relating to a storage medium and a computing platform and claimed subject matter is not limited in these respects.

Although there have been illustrated and described what are presently considered to be example features, it will be understood by those skilled in the art that various other modifications may be made, and equivalents may be substituted, without departing from claimed subject matter. Additionally, many modifications may be made to adapt a particular situation to the teachings of claimed subject matter without departing from central concepts that are described herein. Therefore, it is intended that claimed subject matter not be limited to particular examples disclosed, but that such claimed subject matter may also include all aspects falling within the scope of appended claims, and equivalents thereof.

What is claimed is:

1. An apparatus for use with a plurality of glucose monitoring devices, with a plurality of patients, and with an insulin delivery system, the apparatus comprising:
   one or more processors to:
      obtain a plurality of observations of blood glucose concentrations of the plurality of patients received at the plurality of glucose monitoring devices;
      compute a plurality of profiles of blood glucose concentrations based, at least in part, on the plurality of the observations;
      for the plurality of patients, determine an associated plurality of unidimensional metrics indicative of glycemic health of the plurality of patients, the plurality of unidimensional metrics to be computed based, at least in part, on a convolution of a cost or loss function and the plurality of profiles of blood glucose concentrations of the plurality of patients;
      rank the plurality of patients for treatment according to a triage policy based, at least in part, on the plurality of unidimensional metrics; and
      control the insulin delivery system for balancing hypoglycemic and hyperglycemic tendencies in one of the plurality of patients based, at least in part, on the ranking of the plurality of patients for treatment according to the triage policy.

2. The apparatus of claim 1, wherein the apparatus is further for use with computing platforms co-located with the plurality of patients, and with a communication network, the apparatus further comprising communication interface components to receive information from the communication network,
   wherein the plurality of unidimensional metrics are further to be computed based, at least in part, on messages received through the communication interface components from the computing platforms co-located with the plurality of patients.

3. The apparatus of claim 2, wherein the messages comprise the plurality of blood glucose concentrations.

4. The apparatus of claim 2, wherein the messages comprise the unidimensional metrics computed at the computing platforms co-located with the plurality of patients.

5. An article for use with a plurality of glucose monitoring devices, with a plurality of patients, with an insulin delivery system, and with a special purpose computing apparatus, the article comprising:
a non-transitory storage medium comprising machine-readable instructions stored thereon which are executable by the special purpose computing apparatus to:
obtain a plurality of observations of blood glucose concentrations of the plurality of patients from the plurality of glucose monitoring devices;
compute a plurality of profiles of blood glucose concentrations based, at least in part, on the plurality of the observations;
determine an associated plurality of unidimensional metrics indicative of glycemic health of the plurality of patients, the plurality of unidimensional metrics to be computed based, at least in part, on a convolution of a cost or loss function and the plurality of profiles of blood glucose concentrations of the plurality of patients;
rank the plurality of patients for treatment according to a triage policy based, at least in part, on the plurality of unidimensional metrics; and
control the insulin delivery system to balance hypoglycemic and hyperglycemic tendencies in one of the plurality of patients based, at least in part, on the ranking of the plurality of patients for treatment according to the triage policy.

6. The article of claim 5 wherein the article is further for use with computing platforms co-located with the plurality of patients, and with a communication network, the article further comprising machine-readable instructions that when executed by the special purpose computing apparatus are to:
obtain messages received from the computing platforms co-located with the plurality of patients through the communication network;
wherein the plurality of unidimensional metrics are further to be computed based, at least in part, on the obtained messages.

7. The article of claim 6, wherein the received messages comprise the plurality of blood glucose concentrations.

8. The article of claim 6, wherein the messages comprise the unidimensional metrics computed at the computing platforms co-located with the plurality of patients.

9. A method comprising:
obtaining a plurality of observations of blood glucose concentrations of a plurality of patients using a plurality of glucose monitoring devices;
at a special purpose computing apparatus, computing a plurality of profiles of blood glucose concentrations based, at least in part, on the plurality of the observations;
at the special purpose computing apparatus, for the plurality of patients, determining an associated plurality of unidimensional metrics indicative of glycemic health of the plurality of patients, the plurality of unidimensional metrics being computed based, at least in part, on a convolution of a cost or loss function and the plurality of profiles of blood glucose concentrations of the plurality of patients, the plurality of profiles of blood glucose concentrations being obtained for the plurality of patients under a plurality of predefined therapies; and
controlling, by the special purpose computing apparatus, an insulin delivery system for balancing hypoglycemic and hyperglycemic tendencies in one of the plurality of patients based, at least in part, on ranking by the special purpose computing apparatus of the plurality of predefined therapies,
wherein the ranking the plurality of predefined therapies is based, at least in part, on the plurality of unidimensional metrics.

10. The method of claim 9, wherein the plurality of predefined therapies are defined, at least in part, by closed-loop system design features.

11. The method of claim 9, further comprising:
receiving messages from computing platforms co-located with the plurality of patients through a communication network;
wherein the plurality of unidimensional metrics are further to be computed based, at least in part, on the received messages.

12. The method of claim 11, wherein the received messages comprise the plurality of the observations of the blood glucose concentrations.

13. The method of claim 11, wherein the received messages comprise the unidimensional metrics computed at the computing platforms co-located with the plurality of patients.

* * * * *